US009409934B2

(12) United States Patent
Seth et al.

(10) Patent No.: US 9,409,934 B2
(45) Date of Patent: Aug. 9, 2016

(54) CYCLOHEXENYL NUCLEIC ACIDS ANALOGS

(71) Applicant: Ionis Pharmaceuticals, Inc., Carlsbad, CA (US)

(72) Inventors: Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 145 days.

(21) Appl. No.: 14/069,773

(22) Filed: Nov. 1, 2013

(65) Prior Publication Data

US 2014/0073786 A1    Mar. 13, 2014

Related U.S. Application Data

(62) Division of application No. 13/063,917, filed as application No. PCT/US2009/058011 on Sep. 23, 2009, now Pat. No. 8,604,192.

(60) Provisional application No. 61/150,504, filed on Feb. 6, 2009, provisional application No. 61/099,846, filed on Sep. 24, 2008.

(51) Int. Cl.

| C07D 473/34 | (2006.01) |
|---|---|
| C07D 473/18 | (2006.01) |
| C07D 239/54 | (2006.01) |
| C07D 239/47 | (2006.01) |
| C07F 9/24 | (2006.01) |
| C07H 19/04 | (2006.01) |
| C07H 21/00 | (2006.01) |
| C07F 9/22 | (2006.01) |
| C07F 9/6512 | (2006.01) |
| C07F 9/6561 | (2006.01) |

(52) U.S. Cl.
CPC ............... *C07F 9/24* (2013.01); *C07D 239/47* (2013.01); *C07D 239/54* (2013.01); *C07D 473/18* (2013.01); *C07D 473/34* (2013.01); *C07F 9/22* (2013.01); *C07F 9/65127* (2013.01); *C07F 9/65616* (2013.01); *C07H 19/04* (2013.01); *C07H 21/00* (2013.01)

(58) Field of Classification Search
None
See application file for complete search history.

(56) References Cited

U.S. PATENT DOCUMENTS

| 3,687,808 A | 8/1972 | Merigan et al. |
|---|---|---|
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh et al. |
| 4,973,679 A | 11/1990 | Caruthers et al. |
| 4,981,957 A | 1/1991 | Lableu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederspn et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |

(Continued)

FOREIGN PATENT DOCUMENTS

| WO | WO 94/02499 | 2/1994 |
|---|---|---|
| WO | WO 94/17093 | 8/1994 |

(Continued)

OTHER PUBLICATIONS

Altschul et al., "Basic Local Alignment Search Tool" J. Mol. Biol. (1990) 215:403-410.
Barany et al., "A New Amino Protecting Group Removable by Reduction. Chemistry of the Dithiasuccinoyl (Dts) Function" J. Am. Chem. Soc. (1977) 99:7363-7365.
Barany et al., "Kinetics and Mechanisms of the Thiolytic Removal of the Dithiasuccinoyl (Dts) Amino Protecting Group" J. Am. Chem. Soc. (1980) 102:3084-3095.
Bass, "Double-stranded RNA as a template for gene silencing" Cell (2000) 101:235-238.
Beaucage et al., "Advances in the Synthesis of Oligonucleotides by the Phosphoramidite Approach" Tetrahedron (1992) 48:2223-2311.
(Continued)

*Primary Examiner* — Eric Olson
(74) *Attorney, Agent, or Firm* — McNeill Baur PLLC

(57) ABSTRACT

The present disclosure describes cyclohexenyl nucleic acid analogs, oligomeric compounds prepared therefrom and methods of using the oligomeric compounds. More particularly, cyclohexenyl nucleic acid analogs are provided, having one or more chiral substituents, that are expected to be useful for enhancing properties of oligomeric compounds including nuclease resistance and binding affinity. In some embodiments, the oligomeric compounds provided herein hybridize to a portion of a target RNA resulting in loss of normal function of the target RNA.

20 Claims, No Drawings

(56) References Cited

U.S. PATENT DOCUMENTS

| | | |
|---|---|---|
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,426,220 B1 | 7/2002 | Bennett et al. |
| 6,600,032 B1 | 7/2003 | Manoharan et al. |
| 7,276,592 B2 | 10/2007 | Bergmann et al. |
| 7,399,845 B2 | 7/2008 | Seth et al. |
| 7,427,672 B2 | 9/2008 | Imanishi et al. |
| 2004/0171570 A1 | 9/2004 | Allerson et al. |

FOREIGN PATENT DOCUMENTS

| | | |
|---|---|---|
| WO | WO 99/14226 | 3/1999 |
| WO | WO 01/18003 | 3/2001 |
| WO | WO 01/49687 | 7/2001 |
| WO | WO 02/36743 | 5/2002 |
| WO | WO 2005/012371 | 12/2005 |
| WO | WO 2005/012372 | 12/2005 |
| WO | WO 2006/047842 | 5/2006 |
| WO | WO2006/047842 * | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

Beaucage et al., "The Functionalization of Oligonucleotides via Phosphoramidite Derivatives" Tetrahedron (1993) 49:1925-1963.

Beaucage et al., "The Synthesis of Specific Ribonucleotides and Unrelated Phosphorylated Biomolecules by the Phosphoramidite Method" Tetrahedron (1993) 49:10441-10488.

Bechor et al., "Exocyclic vinyl ethers of ketofuranosides" Tetrahedron (2008) 64(9):2080-2089.

Belikova et al., "Synthesis of Ribonucleosides and Diribonucleoside Phosphates Containing 2-Chloro-Ethylamine and Nitrogen Mustard Residues" Tet. Lett. (1967) 37:3557-3562.

Brazma et al., "Gene expression data analysis" FEBS Letters (2000) 480:17-24.

Carulli et al., "High Throughput Analysis of Differential Gene Expression" J. Cell. Biochem. Suppl. (1998) 30:286-296.

Celts et al., "Gene expression profiling: monitoring transcription and translation products using DNA microarrays and proteomics" FEBS Lett (2000) 480:2-16.

Chiang et al., "Antisense Oligonucleotides Inhibit Intercellular Adhesion Molecule 1 Expression by Two Distinct Mechanisms" J. Biol. Chem. (1991) 266:18162-18171.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Englisch et al., Angewandte Chemie, International Edition (1991) 30:613.

Fire et al., "Potent and Specific Genetic Interference by Double-Stranded RNA in Caenorhabditis Elegans" Nature (1998) 391:806-811.

Fuchs et al., "Identification of Differentially Expressed Genes by Mutually Subtracted RNA Fingerprinting" Anal. Biochem. (2000) 286:91-98.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Going et al., "Molecular Pathology and Future Developments" Eur. J. Cancer (1999) 35:1895-1904.

Gu et al., "Enzymatic Resolution and Base Pairing Properties of d- and 1 -Cyclohexenyl Nucleic Acids (CeNA)" Nucleosides, Nucleotides & Nucleic Acids (2005) 24(5-7):993-998.

(56) References Cited

OTHER PUBLICATIONS

Gu et al., "Base Pairing Properties of D- and L-Cyclohexene Nucleic Acids (CeNA)" Oligonucleotides (2003) 13(6):479-489.
Gu et al., "Synthesis of enantiomeric-pure cyclohexenyo nucleoside building blocks for oligonucleotide synthesis" Tetrahedron (2004) 60(9):2111-2123.
Horvath et al., "Stereoselective synthesis of (—)-ara-cyclohexenyl-adenine" Tetrahedron Letters (2007) 48:3621-3623.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Kroschwitz, The Concise Encyclopedia of Polymer Science and Engineering, pp. 858-859, John Wiley & Sons, 1990.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Madden et al., "Serial analysis of gene expression: from gene discovery to target identification" DDT (2000) 5:415-425.
Montgomery et al., "RNA as a target of double-stranded RNA-mediated genetic interference in Caenorhabditis elegans" Proc Natl. Acad. Sci. (1998) 95:15502-7.
Nauwelaerts et al., "Cyclohexenyl nucleic acids: conformationally flexible oligonucleotides" Nucleic Acids Reseasrch (2005) 33(8):2452-2463.
Nauwelaerts et al., "Structural Characterization and Biological Evaluation of Small Interfering RNAs Containing Cyclohexenyl Nucleosides" J. Am. Chem. Soc. (2007) 129(30):9340-9348.
Nishikura, "A Short Primer on RNAi: RNA-Directed RNA Polymerase Acts as a Key Catalyst" Cell (2001) 107:415-418.
Prashar et al., "READS: A Method for Display of 3'-End Fragment of Restriction Enzyme-Digested cDNAs for Analysis of Differential Gene Expression" Methods Enzymol. (1999) 303:258-272.
Robeyns et al., "Oligonucleotides with cyclohexene-nucleoside building blocks: crystallization and preliminary X-ray studies of a left-handed sequence GTGTACAC" Acta Crystallographica, Section F: Structural Biology and Crystallization Communications (2005) F61(6) 585-586.
Robeyns et al., "Structure of the Fully Modified Left-Handed Cyclohexene Nucleic Acid Sequence GTGTACAC" J. Am. Chem. Soc. (2008) 130(6):1979-1984.
Sanghvi, Antisense Research and Applications, Chapter 15, Crooke & Lebleu ed., CRC Press, 1993.
Scaringe, "RNA Oligonucleotide Synthesis via 5'-Silyl-2'-Orthoester Chemistry" Methods (2001) 23:206-217.
Seth et al., "Synthesis and Antisense Properties of Fluoro Cyclohexenyl Nucleic Acid (F-CeNA), a Nuclease Stable Mimic of 2'-Fluoro RNA" J. Org. Chem. (2012) 77:5074-5085.
Sutcliffe et al., "TOGA: An automated parsing technology for analyzing expression of nearly all genes" PNAS (2000) 97:1976-1981.
Tabara et al., "RNAi in C. elegans: Soaking in the Genome Sequence" Science (1998) 282:430-431.
Takahashi et al., "Synthesis of Cyclophellitol Utilizing a Palladium Chloride Mediated-Ferrier-II Rearrangement" Molecules (2005) 10(8):901-911.
Tijsterman et al., "RNA hellcase MUT-14-dependent gene silencing triggered in C. elegans by short antisense RNAs" Science (2002) 295:694-7.
Timmons et al., "Specific Interference by Ingested dsRNA" Nature (1998) 395:854.
Timmons et al., "Ingestion of bacterially expressed dsRNAs can produce specific and potent genetic interference in Caenorhabditis Elegans" Gene (2001) 263:103-112.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Verbeure et al., "RNase H mediated cleavage of RNA by cyclohexene nucleic acid (CeNA)" Nucleic Acids Research (2001) 29(24):4941-4947.
Wang et al., "Cyclohexene Nucleic Acids (CeNA): Serum Stable Oligonucleotides that Activate RNase H and Increase Duplex Stability with Complementary RNA" J. Am. Chem. (2000) 122:8595-8602.
Wang et al., "A Straightforward Stereoselective Synthesis of d- and 1-5-Hydroxy-4-hydroxymethyl-2-cyclohexenylguanine" J. Org. Chem. (2001) 66:8478-8482.
Wang et al., "Stereocontrolled Synthesis of Ara-Type Cyclohexenyl Nucleosides" J. Org. Chem. (2003) 68:4499-4505.
Wang et al., "Cyclohexene Nucleic Acids (CeNA) Form Stable Duplexes With RNA and Induce Rnase H Activity" Nucleosides, Nucleotides & Nucleic Acids (2001) 20(4-7):785-788.
Wilds et al., "2'-Deoxy 2'-fluoro-β-D-arabinonucleosides and oligonucleotides (2'F-ANA): synthesis and physicochemical studies" Nucleic Acid Research (2000) 28(18):3625-3635.
Zamecnik et al., "Inhibition of Rous sarcoma virus replication and cell transformation by a specific oligodeoxynucleotide" PNAS (1978) 75(1):280-284.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US2009/058011 dated Apr. 3, 2010.

\* cited by examiner

SEQUENCE LISTING

```
<160> NUMBER OF SEQ ID NOS: 5

<210> SEQ ID NO 1
<211> LENGTH: 3160
<212> TYPE: DNA
<213> ORGANISM: H. Sapiens

<400> SEQUENCE: 1 cctccctcg    cccggcgcgg    tcccgtccgc    ctctcgctcg    cctcccgcct    ccctcggtc       60 ttccgaggcg    cccgggctcc    cggcgcggcg    gcggagggg    cgggcaggcc    ggcggcggt      120 gatgtggcag    gactctttat    gcgctgcggc    aggatacgcg    ctcggcgctg    ggacgcgact     180
gcgctcagtt    ctctcctctc    ggaagctgca    gccatgatgg    aagtttgaga    gttgagccgc     240
tgtgaggcga    ggccgggctc    aggcgaggga    gatgagagac    ggcggcggcc    gcggcccgga     300
gcccctctca    gcgcctgtga    gcagccgcgg    gggcagcgcc    ctcggggagc    cggccggcct     360
gcggcggcgg    cagcggcggc    gtttctcgcc    tcctcttcgt    cttttctaac    cgtgcagcct     420
cttcctcggc    ttctcctgaa    agggaaggtg    gaagccgtgg    gctcgggcgg    gagccggctg     480
aggcgcggcg    gcggcggcgg    cggcacctcc    cgctcctgga    gcggggggga    gaagcggcgg     540
cggcggcggc    cgcggcggct    gcagctccag    ggagggggtc    tgagtcgcct    gtcaccattt     600
ccagggctgg    gaacgccgga    gagttggtct    ctcccttct    actgcctcca    acacggcggc     660
ggcggcggcg    gcacatccag    ggacccgggc    cggttttaaa    cctcccgtcc    gccgccgccg     720 cacccccgt    ggcccgggct    ccggaggccg    ccggcggagg    cagccgttcg    gaggattatt     780
cgtcttctcc    ccattccgct    gccgccgctg    ccaggcctct    ggctgctgag    gagaagcagg     840
cccagtcgct    gcaaccatcc    agcagccgcc    gcagcagcca    ttacccggct    gcggtccaga     900
gccaagcggc    ggcagagcga    ggggcatcag    ctaccgccaa    gtccagagcc    atttccatcc     960
tgcagaagaa    gcccgccac    cagcagcttc    tgccatctct    ctcctccttt    ttcttcagcc    1020
```

```
acaggctccc agacatgaca gccatcatca aagagatcgt tagcagaaac aaaaggagat    1080
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataacccac    1320
cacagctaga acttatcaaa cccttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt ttttttatca agagggataa acaccatga    2280 aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatatacctt tttgtgtcaa aaggacattt aaaattcaat taggattaat aaagatggca    2520 cttttcccgtt ttattccagt tttataaaaa gtggagacag actgatgtgt atacgtagga    2580 atttttttcct tttgtgttct gtcaccaact gaagtggcta aagagctttg tgatatactg    2640
gttcacatcc taccccttttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                         3160

<210> SEQ ID NO 2
<211> LENGTH: 26
<212> TYPE: DNA
<213> ORGANISM: Artificial Sequence
<220> FEATURE:
<223> OTHER INFORMATION: Primer
```

```
<400> SEQUENCE: 2
aatggctaag tgaagatgac aatcat                                          26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                           25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                      30

<210> SEQ ID NO 5
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 5
tcttagcact ggcctt                                                     16
```

CYCLOHEXENYL NUCLEIC ACIDS ANALOGS

CROSS REFERENCED TO RELATED APPLICATIONS

This application is a divisional of U.S. application Ser. No. 13/063,917, filed Mar. 14, 2011, which is a U.S. National Phase filing under 35 U.S.C. 371 claiming priority to International Serial No. PCT/US2009/058011 filed Sep. 23, 2009, which claims priority under 35 USC 119(e) to U.S. Provisional Ser. No. 61/099,846, filed Sep. 24, 2008 and to U.S. Provisional Ser. No. 61/150,504, filed Feb. 6, 2009, each of which is incorporated herein by reference in its entirety.

SEQUENCE LISTING

The present application is being filed along with a Sequence Listing in electronic format. The Sequence Listing is provided as a file entitled CHEM0054USD1SEQ.txt, created on Nov. 1, 2013 which is 8 Kb in size. The information in the electronic format of the sequence listing is incorporated herein by reference in its entirety.

FIELD OF THE INVENTION

Provided herein are novel cyclohexenyl nucleic acid analogs, oligomeric compounds prepared therefrom and methods of using the oligomeric compounds. More particularly, the cyclohexenyl nucleic acid analogs provided herein have a cyclohexene ring system, replacing the furanose ring in naturally occurring nucleosides, that is substituted with at least one halogen atom at the 2'-position and may comprise further substituent groups. In certain embodiments, the oligomeric compounds hybridize to a portion of a target RNA resulting in loss of normal function of the target RNA.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with an antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example affinity and nuclease resistance. One such group of chemically modified nucleosides includes cyclohexenyl nucleic acids wherein the furanose ring in naturally occurring nucleosides, is replaced with a cyclohexenyl ring.

Cyclohexenyl nucleic acids and analogs thereof have been reported in the scientific and patent literature as monomers as well as in oligomeric compounds, see for example: Robeyns et al., *J. Am. Chem. Soc.*, 2008, 130(6), 1979-1984; Horváth et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety.

Consequently, there remains an ongoing need for agents that specifically regulate gene expression via antisense mechanisms. Disclosed herein are cyclohexenyl nucleic acid analogs that are expected to be useful in the preparation of antisense compounds for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are novel cyclohexenyl nucleic acid analogs, oligomeric compounds prepared therefrom and methods of using the oligomeric compounds. More particularly, the cyclohexenyl nucleic acid analogs (herein referred to as CeNA analogs) provided herein have a cyclohexene ring system, replacing the furanose ring in naturally occurring nucleosides, that is substituted with at least one halogen atom at the 2'-position and may comprise further substituent groups. In certain embodiments, the oligomeric compounds hybridize to a portion of a target RNA resulting in loss of normal function of the target RNA.

The variables are defined individually in further detail herein. It is to be understood that the CeNA analogs, oligomeric compounds, and methods of use thereof provided herein include all combinations of the embodiments disclosed and variables defined herein.

In certain embodiments, CeNA analogs are provided herein having Formula I:

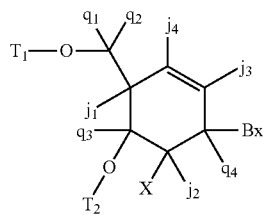

wherein:

Bx is a heterocyclic base moiety;

X is halogen;

one of $T_1$ and $T_2$ is H or a hydroxyl protecting group and the other of $T_1$ and $T_2$ is H, a hydroxyl protecting group or a reactive phosphorus group;

$q_1$, $q_2$, $q_3$ and $q_4$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$j_1$, $j_2$, $j_3$ and $j_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl; and wherein each substituted group is, independently, mono or poly substituted with optionally protected substituent groups independently selected from halogen, oxo, hydroxyl, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl.

In certain embodiments, at least one of $q_1$, $q_2$, $q_3$ and $q_4$ is $C_1$-$C_6$ alkyl or substituted $C_1$-$C_6$ alkyl. In certain embodiments, at least one of $q_1$, $q_2$, $q_3$ and $q_4$ is substituted $C_1$-$C_6$ alkyl. In certain embodiments, at least one of $q_1$, $q_2$, $q_3$ and $q_4$ is substituted $C_1$-$C_6$ alkyl comprising at least one substituent group selected from fluoro or $OCH_3$. In certain embodiments, at least one of $q_1$, $q_2$, $q_3$ and $q_4$ is $C_1$-$C_6$ alkyl. In certain embodiments, at least one of $q_1$, $q_2$, $q_3$ and $q_4$ is methyl.

In certain embodiments, at least one of $j_1$, $j_2$, $j_3$ and $j_4$ is halogen, $C_1$-$C_6$ alkyl or substituted $C_1$-$C_6$ alkyl. In certain embodiments, at least one of $j_1$, $j_2$, $j_3$ and $j_4$ is substituted $C_1$-$C_6$ alkyl. In certain embodiments, at least one of $j_1$, $j_2$, $j_3$ and $j_4$ is substituted $C_1$-$C_6$ alkyl comprising at least one substituent group selected from fluoro or $OCH_3$. In certain embodiments, at least one of $j_1$, $j_2$, $j_3$ and $j_4$ is $C_1$-$C_6$ alkyl. In certain embodiments, at least one of $j_1$, $j_2$, $j_3$ and $j_4$ is methyl. In certain embodiments, at least one of $j_1$, $j_2$, $j_3$ and $j_4$ is fluoro.

In certain embodiments, X is fluoro. In certain embodiments, X and $J_2$ are each fluoro.

In certain embodiments, X is fluoro and $q_1$, $q_2$, $q_3$, $q_4$, $j_1$, $j_2$, $j_3$ and $j_4$ are each H.

In certain embodiments, CeNA analogs are provided herein having Formula II:

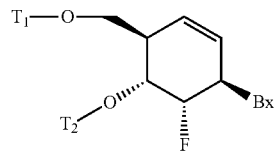

wherein:

Bx is a heterocyclic base moiety; and one of $T_1$ and $T_2$ is H or a hydroxyl protecting group and the other of $T_1$ and $T_2$ is H, a hydroxyl protecting group or a reactive phosphorus group.

In certain embodiments, CeNA analogs are provided comprising one or more hydroxyl protecting groups ($T_1$ and or $T_2$), independently, selected from benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, $T_1$ is selected from acetyl, benzyl, t-butyldimethylsilyl, t-butyldiphenylsilyl and dimethoxytrityl. In certain embodiments, $T_1$ is 4,4'-dimethoxytrityl.

In certain embodiments, $T_2$ is a reactive phosphorus group. In certain embodiments, $T_2$ is a reactive phosphorus group selected from diisopropylcyanoethoxy phosphoramidite and H-phosphonate.

In certain embodiments, $T_1$ is 4,4'-dimethoxytrityl and $T_2$ is diisopropylcyanoethoxy phosphoramidite.

In certain embodiments, oligomeric compounds are provided comprising at least one CeNA analog having Formula III:

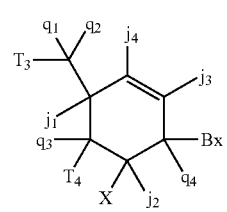

wherein independently for each CeNA analog having Formula III:

Bx is a heterocyclic base moiety;

X is halogen;

$T_3$ and $T_4$ are each, independently, hydroxyl, a protected hydroxyl, a linked conjugate group or an internucleoside linking group attaching the CeNA analog to the oligomeric compound wherein at least one of $T_3$ and $T_4$ is an internucleoside linking group attaching the CeNA analog to the oligomeric compound;

$q_1$, $q_2$, $q_3$ and $q_4$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$j_1$, $j_2$, $j_3$ and $j_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl; and wherein each substituted group is, independently, mono or poly substituted with optionally protected substituent groups independently selected from halogen, oxo, hydroxyl, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl.

In certain embodiments, oligomeric compounds are provided comprising at least one CeNA analog having Formula III wherein at least one of $q_1$, $q_2$, $q_3$ and $q_4$ is $C_1$-$C_6$ alkyl or substituted $C_1$-$C_6$ alkyl for essentially each CeNA analog having Formula III. In certain embodiments, at least one of $q_1$, $q_2$, $q_3$ and $q_4$ is substituted $C_1$-$C_6$ alkyl for essentially each CeNA analog having Formula III. In certain embodiments, the substituted $C_1$-$C_6$ alkyl groups comprises at least one substituent group selected from fluoro and $OCH_3$. In certain embodiments, at least one of $q_1$, $q_2$, $q_3$ and $q_4$ is $C_1$-$C_6$ alkyl for essentially each CeNA analog having Formula III. In certain embodiments, each of the $C_1$-$C_6$ alkyl groups is methyl.

In certain embodiments, oligomeric compounds are provided comprising at least one CeNA analog having Formula III wherein at least one of $j_1$, $j_2$, $j_3$ and $j_4$ is halogen, $C_1$-$C_6$ alkyl or substituted $C_1$-$C_6$ alkyl for essentially each CeNA analog having Formula III. In certain embodiments, at least one of $j_1, j_2, j_3$ and $j_4$ is substituted $C_1$-$C_6$ alkyl for essentially each CeNA analog having Formula III. In certain embodiments, each of the substituted $C_1$-$C_6$ alkyl groups comprises at least one substituent group selected from fluoro and $OCH_3$. In certain embodiments, at least one of $j_1, j_2, j_3$ and $j_4$ is $C_1$-$C_6$ alkyl for essentially each CeNA analog having Formula III. In certain embodiments, each of the $C_1$-$C_6$ alkyl groups is methyl. In certain embodiments, at least one of $j_1, j_2, j_3$ and $j_4$ is fluoro for essentially each CeNA analog having Formula III.

In certain embodiments, oligomeric compounds are provided comprising at least one CeNA analog having Formula III wherein X is fluoro for essentially each CeNA analog having Formula III. In certain embodiments, oligomeric compounds are provided comprising at least one CeNA analog having Formula III wherein X and $J_2$ are each fluoro for essentially each CeNA analog having Formula III.

In certain embodiments, oligomeric compounds are provided comprising at least one CeNA analog having Formula III wherein X is fluoro and $q_1, q_2, q_3, q_4, j_1, j_2, j_3$ and $j_4$ are each H for essentially each CeNA analog having Formula III.

In certain embodiments, oligomeric compounds are provided comprising at least one CeNA analog wherein each CeNA analog has Formula IV:

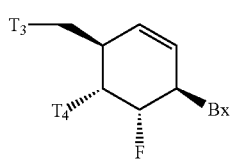

IV wherein:
Bx is a heterocyclic base moiety; and
$T_3$ and $T_4$ are each, independently, hydroxyl, a protected hydroxyl, a linked conjugate group or an internucleoside linking group attaching the CeNA analog to the oligomeric compound wherein at least one of $T_3$ and $T_4$ is an internucleoside linking group attaching the CeNA analog to the oligomeric compound.

In certain embodiments, oligomeric compounds are provided comprising at least one CeNA analog having Formula III wherein each internucleoside linking group is, independently, selected from phosphodiester or phosphorothioate. In certain embodiments, each internucleoside linking group is a phosphorothioate.

In certain embodiments, oligomeric compounds are provided comprising at least one CeNA analog having Formula IV wherein each internucleoside linking group is, independently, selected from phosphodiester or phosphorothioate. In certain embodiments, each internucleoside linking group is a phosphorothioate.

In certain embodiments, oligomeric compounds are provided comprising at least one region having at least 2 contiguous cyclohexenyl nucleic acid analogs having Formula III. In certain embodiments, oligomeric compounds are provided comprising at least two regions wherein each region independently comprises at least 2 contiguous cyclohexenyl nucleic acid analogs having Formula III wherein the two regions are separated by at least one β-D-2'-deoxyribonucleoside. In certain embodiments, oligomeric compounds are provided comprising at least two regions wherein each region independently comprises from 1 to about 5 contiguous cyclohexenyl nucleic acid analogs having Formula III and wherein the two regions are separated by an internal region comprising at least one monomer subunit wherein each monomer subunit is, independently, a nucleoside or a modified nucleoside.

In certain embodiments, gapped oligomeric compounds are provided comprising two regions of contiguous cyclohexenyl nucleic acid analogs having Formula III wherein one of said at least two regions of contiguous cyclohexenyl nucleic acid analogs having Formula III is located at the 5'-end and the other of said at least two regions of contiguous cyclohexenyl nucleic acid analogs having Formula III is located at the 3'-end and wherein the two regions are separated by an internal region comprising from about 6 to about 18 monomer subunits wherein each monomer subunit is, independently, a nucleoside or a modified nucleoside.

In certain embodiments, gapped oligomeric compounds are provided comprising an internal region of from about 8 to about 14 contiguous β-D-2'-deoxyribofuranosyl nucleosides. In certain embodiments, gapped oligomeric compounds are provided comprising an internal region of from about 9 to about 12 contiguous β-D-2'-deoxyribofuranosyl nucleosides.

In certain embodiments, oligomeric compounds are provided comprising at least one region of at least two contiguous CeNA analogs having Formula III. In certain embodiments, oligomeric compounds are provided comprising at least two regions wherein each region independently comprises at least two contiguous CeNA analogs having Formula III. In certain embodiments, gapped oligomeric compounds are provided comprising at least two regions wherein each region independently comprises at least two contiguous CeNA analogs having Formula III. In certain embodiments, gapped oligomeric compounds are provided comprising at least two regions wherein each region independently comprises at least two contiguous CeNA analogs having Formula III and wherein the gapped oligomeric compound further comprises at least one region of from about 8 to about 14 or from about 9 to about 12 contiguous β-D-2'-deoxyribofuranosyl nucleosides.

In certain embodiments, oligomeric compounds are provided comprising one region of from 2 to three contiguous CeNA analogs having Formula III, an optional second region of 1 or 2 contiguous CeNA analogs having Formula III and a third region of from 8 to 14β-D-2'-deoxyribofuranosyl nucleosides wherein the third region is located between the first and the second regions.

In certain embodiments, oligomeric compounds are provided comprising from about 8 to about 40 monomer subunits. In certain embodiments, oligomeric compounds are provided comprising from about 8 to about 20 monomer subunits. In certain embodiments, oligomeric compounds are provided comprising from about 10 to about 16 monomer subunits. In certain embodiments, oligomeric compounds are provided comprising from about 10 to about 14 monomer subunits.

In certain embodiments, oligomeric compounds are provided comprising at least one CeNA analog of Formula III wherein for each of the CeNA analogs, $q_1, q_2, q_3, q_4, j_1, j_2, j_3, j_4$ and X are uniformly modified. The term uniformly modified, as it applies here, means that the variables $q_1, q_2, q_3, q_4, j_1, j_2, j_3, j_4$ and X each, independently, have the same substituent group and further have the same stereochemistry for each of the CeNA analogs within the oligomeric compound. The term doesn't apply to the heterocyclic bases, internucleoside linkages or restrict the use of other groups such as terminal groups.

In certain embodiments, methods are provided comprising contacting a cell in an animal with one or more of the oligomeric compounds provided herein. In certain embodiments, the cell is in a human. In certain embodiments, the oligomeric compound is complementary to a target RNA. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the methods further comprise evaluating the activity of the oligomeric compound on the cell. In certain embodiments, the evaluating comprises detecting the levels of target RNA. In certain embodiments, the evaluating comprises detecting the levels of a protein. In certain embodiments, the evaluating comprises detection of one or more phenotypic effects.

In certain embodiments, oligomeric compounds are provided for use in therapy. In certain embodiments, the therapy is treating a disease characterized by undesired gene expression. In certain embodiments, the therapy is treating a disease by inhibiting gene expression.

In certain embodiments, oligomeric compounds are provided for contacting a cell in an animal.

In certain embodiments, oligomeric compounds are provided for use in the manufacture of a medicament for the treatment of a disease characterized by undesired gene expression.

In certain embodiments, oligomeric compounds are provided for use in the manufacture of a medicament for treating a disease by inhibiting gene expression.

In certain embodiments, a pharmaceutical composition is provided comprising an oligomeric compound provided herein and a pharmaceutically acceptable carrier.

DETAILED DESCRIPTION OF THE INVENTION

Provided herein are novel cyclohexenyl nucleic acid (CeNA) analogs, oligomeric compounds that include these CeNA analogs and methods of using the oligomeric compounds. Also included are intermediates and methods for preparing the CeNA analogs and incorporating them into oligomeric compounds. More particularly, the CeNA analogs provided herein have a cyclohexene ring system, replacing the furanose ring in naturally occurring nucleosides, that is substituted with at least one halogen atom at the 2'-position and may comprise further substituent groups. The CeNA analogs are expected to be useful for enhancing one or more properties of the oligomeric compounds they are incorporated into such as for example nuclease resistance. In certain embodiments, the oligomeric compounds provided herein hybridize to a portion of a target RNA resulting in loss of normal function of the target RNA. In a more general embodiment, antisense oligomeric compounds are prepared comprising at least one of the CeNA analogs provided herein that are useful for reducing target RNA, such as messenger RNA, in vitro and in vivo. In one aspect the reduction of target RNA is useful for inhibition of gene expression via numerous pathways. Such pathways include for example the steric blocking of transcription or translation and cleavage of mRNA via single or double stranded oligomeric compounds. The oligomeric compounds provided herein are also expected to be useful as primers and probes in diagnostic applications. In certain embodiments, oligomeric compounds comprising at least one of the CeNA analogs provided herein are expected to be useful as aptamers which are oligomeric compounds capable of binding to aberrant proteins in an in vivo setting.

The CeNA analogs provided herein are prepared as monomers which are incorporated at one or more positions of an oligomeric compound and are generally described by Formula Ia:

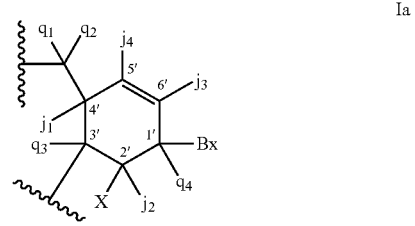

wherein:
Bx is a heterocyclic base moiety;
X is halogen;
$q_1$, $q_2$, $q_3$ and $q_4$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
$j_1$, $j_2$, $j_3$ and $j_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl; and
wherein each substituted group is, independently, mono or poly substituted with optionally protected substituent groups independently selected from halogen, oxo, hydroxyl, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl.

The squiggly lines indicate attachment of the CeNA analogs to groups and/or an oligomeric compound which is defined more specifically throughout the present disclosure.

In certain embodiments, oligomeric compounds provided herein include at least one CeNA analog described by Formula III:

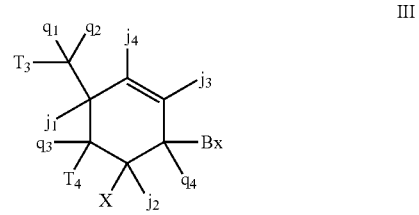

wherein independently for each CeNA analog having Formula III:
Bx is a heterocyclic base moiety;
X is halogen;
$T_3$ and $T_4$ are each, independently, hydroxyl, a protected hydroxyl, a linked conjugate group or an internucleoside linking group attaching the CeNA analog to the oligomeric compound wherein at least one of $T_3$ and $T_4$ is an internucleoside linking group attaching the CeNA analog to the oligomeric compound;
$q_1$, $q_2$, $q_3$ and $q_4$ are each, independently, H $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
$j_1$, $j_2$, $j_3$ and $j_4$ are each, independently, H halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl; and
wherein each substituted group is, independently, mono or poly substituted with optionally protected substituent groups independently selected from halogen, oxo, hydroxyl, $OJ_1$, NJ₁J₂, SJ₁, N₃, OC(=O)J₁ and CN, wherein each J₁ and J₂ is, independently, H or C₁-C₆ alkyl.

In certain embodiments, the 2'-halogen group is prepared having particular stereochemistry (R or S). In certain embodiments, the 2'-halogen group is prepared as a mixture of R and S. In certain embodiments, CeNA analogs having Formula III are prepared wherein each of the bonds/substituents have a specific, predefined stereochemistry.

In certain embodiments, CeNA analogs are incorporated at one or more positions within an oligomeric compound wherein essentially each of such CeNA analogs have Formula IV:

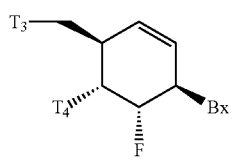

wherein:
Bx is a heterocyclic base moiety; and
T₃ and T₄ are each, independently, hydroxyl, a protected hydroxyl, a linked conjugate group or an internucleoside linking group attaching the CeNA analog to the oligomeric compound wherein at least one of T₃ and T₄ is an internucleoside linking group attaching the CeNA analog to the oligomeric compound.

In certain embodiments, the CeNA analogs provided herein are useful for modifying oligomeric compounds at one or more positions. Such modified oligomeric compounds can be described as having a particular motif. In certain embodiments, the motifs include without limitation, a gapped motif, a hemimer motif, a blockmer motif, a uniformly fully modified motif, a positionally modified motif and an alternating motif. In conjunction with these motifs a wide variety of internucleoside linkages can also be used including but not limited to phosphodiester and phosphorothioate internucleoside linkages which can be incorporated uniformly or in combinations. The positioning of the CeNA analogs provided herein and the use of linkage strategies can be easily optimized to enhance activity for a selected target.

The term "motif" refers to the pattern created by the relative positioning of monomeric subunits within an oligomeric compound wherein the pattern is determined by comparing the sugar groups. As used herein the term "sugar group" as it applies to motifs includes naturally occurring sugars having a furanose ring, sugars having a modified furanose ring and sugar surrogates wherein the furanose ring has been replaced with another ring system such as the cyclohexenyl ring system used in the CeNA analogs provided herein. When each sugar group is the same (DNA, RNA, modified or surrogate) the motif is termed uniformly fully modified. When two or more types of sugar groups are present the motif is defined by the pattern created from the positioning of monomeric subunits having one type of sugar group relative to the positioning of monomeric subunits having different types of sugar groups within an oligomeric compound. Illustrative examples of some different types of sugar groups useful in the preparation of oligomeric compounds having motifs include without limitation β-D-ribose, β-D-2'-deoxyribose, 2'-substituted sugars (such as 2'-methoxyethoxy), 4'-S-sugars (such as 4'-S-ribose, 4'-S-2'-deoxyribose and 4'-S-2'-substituted ribose), bicyclic modified sugars (such as LNA's having a 2'-O—CH₂-4' bridging group) and sugar surrogates (such as the CeNA analogs provided herein). The type of heterocyclic base and internucleoside linkage used at each position is variable and is not a factor in determining the motif. The presence of one or more other groups including but not limited to capping groups, conjugate groups and other 5' or 3'-terminal groups is also not a factor in determining the motif Representative U.S. patents that teach the preparation of motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomeric subunits that have different sugar groups, each L is an internucleoside linking group, n is from about 4 to about 12 and nn is 0 or 1. This permits alternating oligomeric compounds from about 9 to about 26 monomer subunits in length. This length range is not meant to be limiting as longer and shorter oligomeric compounds are also amenable to the present invention. In certain embodiments, one of A and B is a CeNA analog as provided herein.

As used herein the term "uniformly fully modified motif" refers to an oligomeric compound comprising a contiguous sequence of linked monomer subunits that each have the same type of sugar group. In certain embodiments, the uniformly fully modified motif includes a contiguous sequence of CeNA analogs. In certain embodiments, one or both of the 3' and 5'-ends of the contiguous sequence of CeNA analogs, comprise terminal groups such as one or more unmodified nucleosides.

As used herein the term "hemimer motif" refers to an oligomeric compound having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomeric subunits) having uniform but different sugar groups and located on either the 3' or the 5' end of the oligomeric compound. In certain embodiments, the hemimer motif comprises a contiguous sequence of from about 10 to about 28 monomer subunits of one type with from 1 to 5 or from 2 to about 5 monomer subunits of a second type located at one of the termini. In certain embodiments the hemimer is a contiguous sequence of from about 8 to about 20β-D-2'-deoxyribonucleosides having from 1-12 contiguous CeNA analogs located at one of the termini. In certain embodiments the hemimer is a contiguous sequence of from about 8 to about 20 β-D-2'-deoxyribonucleosides having from 1-5 contiguous CeNA analogs located at one of the termini. In certain embodiments the hemimer is a contiguous sequence of from about 12 to about 18 β-D-2'-deoxyribonucleosides having from 1-3 contiguous CeNA analogs located at one of the termini. In certain embodiments the hemimer is a contiguous sequence of from about 10 to about 14 β-D-2'-deoxyribonucleosides having from 1-3 contiguous CeNA analogs located at one of the termini.

As used herein the term "blockmer motif" refers to an oligomeric compound comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In certain embodiments, blockmer oligomeric compounds are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In certain embodiments, each of the two or more regions have the same type of sugar group. In certain embodiments, each of the two or more regions have a different type of sugar group. In certain embodiments, positionally modified oligomeric compounds are provided comprising a sequence of from 8 to 20 β-D-2'-deoxyribonucleosides that further includes two or three regions of from 2 to about 5 contiguous CeNA analogs each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar groups with the internal region comprising β-D-2'-deoxyribonucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups.

In certain embodiments, the gapped oligomeric compounds comprise an internal region of β-D-2'-deoxyribonucleosides with one of the external regions comprising CeNA analogs as disclosed herein. In certain embodiments, the gapped oligomeric compounds comprise an internal region of β-D-2'-deoxyribonucleosides with both of the external regions comprising CeNA analogs as disclosed herein. In certain embodiments, the gapped oligomeric compounds comprise an internal region of β-D-2'-deoxyribonucleosides with both of the external regions comprising CeNA analogs selected from Formula III or IV. In certain embodiments, gapped oligomeric compounds are provided herein wherein all of the monomer subunits comprise non-naturally occurring sugar groups.

In certain embodiments, gapped oligomeric compounds are provided comprising one or two CeNA analogs at the 5'-end, two or three CeNA analogs at the 3'-end and an internal region of from 10 to 16 β-D-2'-deoxyribonucleosides. In certain embodiments, gapped oligomeric compounds are provided comprising one CeNA analog at the 5'-end, two CeNA analogs at the 3'-end and an internal region of from 10 to 16 β-D-2'-deoxyribonucleosides. In certain embodiments, gapped oligomeric compounds are provided comprising one CeNA analog at the 5'-end, two CeNA analogs at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—NR$_{bb}$R$_{cc}$), imino (=NR$_{bb}$), amido (—C(O)NR$_{bb}$R$_{cc}$ or —N(R$_{bb}$)C(O)R$_{aa}$), azido (—N$_3$), nitro (—NO$_2$), cyano (—CN), carbamido (—OC(O)NR$_{bb}$R$_{cc}$ or —N(R$_{bb}$)—C(O)OR$_{aa}$), ureido (—N(R$_{bb}$)C(O)NR$_{bb}$R$_{cc}$), thioureido (—N(R$_{bb}$)C(S)NR$_{bb}$R$_{cc}$), guanidinyl (—N(R$_{bb}$)—C(=NR$_{bb}$)NR$_{bb}$R$_{cc}$), amidinyl (—C(=NR$_{bb}$)NR$_{bb}$R$_{cc}$ or —N(R$_{bb}$)C(NR$_{bb}$)R$_{aa}$), thiol (—SR$_{bb}$), sulfonyl (—S(O)R$_{bb}$), sulfonyl (—S(O)$_2$R$_{bb}$), sulfonamidyl (—S(O)$_2$NR$_{bb}$R$_{cc}$ or —N(R$_{bb}$)S(O)$_2$R$_{bb}$) and conjugate groups. Wherein each R$_{aa}$, R$_{bb}$ and R$_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butyryl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

The term "heteroarylalkyl," as used herein, refers to a heteroaryl group as previously defined having an alky radical is used to attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems that are single or polycyclic wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In certain embodiments, mono or poly cyclic structures can be attached to a parent molecule directly through a ring atom, through a substituent group or a bifunctional linking moiety.

The term "oxo" refers to the group (=O).

The terms "bicyclic nucleic acid (BNA)" and "bicyclic nucleoside" refer to a nucleoside wherein the furanose portion of the nucleoside includes a bridge connecting two carbon atoms on the furanose ring, thereby forming a bicyclic ring system.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Linking groups or bifunctional linking moieties such as those known in the art are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glycols or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, oligomeric compounds are modified by covalent attachment of one or more 5' or 3'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmacokinetics or pharmacodynamics of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

In certain embodiments, oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

The term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In certain embodiments, oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The inter-mediate phosphite compounds are subsequently oxidized to the $P^V$ state using known methods to yield, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-$CH_2$—C(=O)—N(H)-5'), amide-4 (3'-$CH_2$—N(H)—C(=O)-5').

In certain embodiments, oligomeric compounds are provided containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In certain embodiments, oligomeric compounds are provided having one or more internucleoside linkages that don't contain a phosphorus atom. Such oligomeric compounds include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In the context of this invention, the term "oligonucleoside" refers to a sequence of two or more nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

As used herein the phrase "neutral internucleoside linkage" is intended to include internucleoside linkages that are non-ionic. Neutral internucleoside linkages include but are not limited to phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and $CH_2$ component parts.

The compounds described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In general, the term "oligomeric compound" refers to a contiguous sequence of linked monomeric subunits. In general each linked monomeric subunits is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups. When preparing oligomeric compounds having specific motifs as disclosed herein it can be advantageous to mix non-naturally occurring monomer subunits such as the CeNA analogs as provided herein with other non-naturally occurring monomer subunits, naturally occurring monomer subunits (nucleosides) or mixtures thereof. In certain embodiments, oligomeric compounds are provided herein comprising a contiguous sequence of linked monomeric subunits wherein at least one monomeric subunit is a CeNA analog as provided herein. In certain embodiments, oligomeric compounds are provided comprising a plurality of CeNA analogs as provided herein.

Oligomeric compounds are routinely prepared linearly but can also be joined or otherwise prepared to be circular and/or can be prepared to include branching. Oligomeric compounds can form double stranded constructs such as for example two strands hybridized to form double stranded compositions. The double stranded compositions can be linked or separate and can include various other groups such as conjugates and/or overhangs on the ends.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference. The term "nucleobase" or "heterocyclic base moiety" as used herein, is intended to by synonymous with "nucleic acid base or mimetic thereof." In general, a nucleobase or heterocyclic base moiety is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The *Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

The heterocyclic base moiety of each of the CeNA analogs can be modified with one or more substituent groups to enhance one or more properties such as affinity for a target strand or affect some other property in an advantageous manner. Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Oligomeric compounds provided herein can optionally contain one or more nucleosides wherein the sugar group has been modified. Such sugar modified nucleosides may impart enhanced nuclease stability, increased binding affinity or some other beneficial biological property to the oligomeric compounds. As used herein the term "modified sugar" refers to modifications that can be made to the furanose sugar portion of otherwise unmodified or modified nucleosides useful herein. Such modified sugars include without limitation substitution with one or more substituent groups, bridging of two non-geminal ring carbon atoms to form a bicyclic nucleoside or substitution of the 4'-O atom with a disubstituted methylene group [$C(R)_2$] or a heteroatom or substituted heteroatom (NR). Modified sugar moieties can also comprise mixtures of these modifications such as for example putting a 5'-substituent group on a bicyclic nucleoside.

Examples of substituent groups useful for modifying sugar moieties of nucleosides include without limitation 2'-F, 2'-allyl, 2'-amino, 2'-azido, 2'-thio, 2'-O-allyl, 2'-$OCF_3$, 2'-O—$C_1$-$C_{10}$ alkyl, 2'-O—$CH_3$, $OCF_3$, 2'-O—$CH_2CH_3$, 2'-O—$(CH_2)_2CH_3$, 2'-O—$(CH_2)_2$—O—$CH_3$, 2'-O$(CH_2)_2SCH_3$, 2'-O—$CH_2$—CH=$CH_2$ (MOE), 2'-O—$(CH_2)_3$—$N(R_m)(R_n)$, 2'-O—$(CH_2)_2$—O—$N(R_m)(R_n)$, 2'-O—$(CH_2)_2$—O—$(CH_2)_2$—$N(R_m)(R_n)$, 2'-O—$CH_2C$(=O)—$N(R_m)(R_n)$, 2'-O—$CH_2C$(=O)—N(H)—$(CH_2)_2$—$N(R_m)(R_n)$ and 2'-O—$CH_2$—N(H)—C(=$NR_m$)[$N(R_m)(R_n)$], 5'-vinyl, 5'-methyl (R or S) and 4'-S wherein each $R_m$ and $R_n$ is, independently, H, substituted or unsubstituted $C_1$-$C_{10}$ alkyl or a protecting group. Further examples of modified sugar moieties include without limitation bicyclic sugars (e.g. bicyclic nucleic acids or bicyclic nucleosides discussed below).

Combinations of these modifications are also provided for herein without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the terms "bicyclic nucleic acid" and "bicyclic nucleoside" refer to nucleosides wherein the sugar portion of the nucleoside is bicyclic (e.g. bicyclic sugar). In certain embodiments, a bicyclic nucleic acid comprises a nucleoside wherein the furanose ring comprises a bridge between two non-geminal ring carbon atoms. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(=CH$_2$)-2' (and analogs thereof see published International Application WO 2008/154401, published on Dec. 8, 2008). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated as is the case with the non-ring system used in peptide nucleic acid. The term is meant to include replacement of the sugar group with all manner of sugar surrogates know in the art and includes without limitation sugar surrogate groups such as morpholinos, cyclohexenyls and cyclohexitols. In most monomer subunits having a sugar surrogate group the heterocyclic base moiety is generally maintained to permit hybridization.

In certain embodiments, nucleosides having sugar surrogate groups include without limitation, replacement of the ribosyl ring with a surrogate ring system such as a tetrahydropyranyl ring system (also referred to as hexitol) as illustrated below:

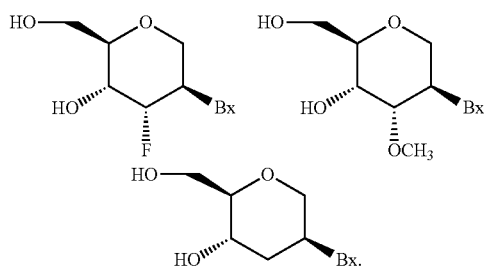

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J.). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

As used herein the term "nucleoside mimetic" is intended to include those structures used to replace the sugar or the sugar and the base and not necessarily the linkage at one or more positions of an oligomeric compound such as for example nucleoside mimetics having morpholino or bicyclo [3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The CeNA analogs provided herein are illustrative of an example of a sugar surrogate wherein the furanose sugar group has been replaced with a cyclohexenyl ring system. The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base but abasic modified nucleosides are also envisioned. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar group has a 2'-O—CHR$_a$-4' bridging group, wherein R$_a$ is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as a base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribnucleosides, 2'-substituted nucleosides, 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic ribonucleosides wherein the ribose sugar group has a 2'-O—CHR$_a$-4' bridging group, wherein R$_a$ is H, alkyl or substituted alkyl), nucleoside mimetics and nucleosides having sugar surrogates (such as the CeNA analogs provided herein).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the CeNA analogs provided herein and may also include other monomer subunits including but not limited to nucleosides, modified nucleosides, nucleosides comprising sugar surrogate groups and nucleoside mimetics.

In certain embodiments, oligomeric compounds provided herein comprise from about 8 to about 80 monomer subunits in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 10 to 16 monomer subunits in length. One having ordinary skill in the art will appreciate that this embodies oligomeric compounds of 10, 11, 12, 13, 14, 15 or 16 monomer subunits in length, or any range therewithin.

In certain embodiments, oligomeric compounds provided herein comprise from about 12 to 16 monomer subunits in length. One having ordinary skill in the art will appreciate that this embodies oligomeric compounds of 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds of any of a variety of ranges of lengths of linked monomer subunits are provided. In certain embodiments, oligomeric compounds are provided consisting of X—Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, ranges for the length of the oligomeric compounds provided herein are 8-16, 8-40, 10-12, 10-14, 10-16, 10-18, 10-20, 10-21, 12-14, 12-16, 12-18, 12-20 and 12-24 linked monomer subunits.

In certain embodiments, the ranges for the oligomeric compounds listed herein are meant to limit the number of monomer subunits in the oligomeric compounds, however such oligomeric compounds may further include protecting groups such as hydroxyl protecting groups, optionally linked conjugate groups, 5' and/or 3'-terminal groups and/or other substituents.

In certain embodiments, oligomerization of modified and unmodified nucleosides and mimetics thereof, is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]-methyl (2'-O—$CH_2$—O—$Si(iPr)_3$ (TOM), and the 5'-O-silyl ether-2'-ACE (5'-O-bis(trimethylsiloxy)-cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS=5'-O-DMT-2'-O-t-butyldimethylsilyl; TOM=2'-O-[(triisopropylsilyl)oxy]methyl; DOD/ACE=(5'-O-bis(trimethylsiloxy)cyclododecyloxysilyl ether-2'-O-bis (2-acetoxyethoxy)methyl; and FPMP=5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In the context of this invention, "hybridization" means the pairing of complementary strands of oligomeric compounds. In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent.

Suitable target segments may also be combined with their respective complementary antisense oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds provided herein can also be applied in the areas of drug discovery and target validation. In certain embodiments, provided here is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype. In certain embodiments, there is provided oligomeric compounds of the invention for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While in certain embodiments, oligomeric compounds provided herein can be utilized as described, the following examples serve only to illustrate and are not intended to be limiting.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M $NH_4OAc$ solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M $NH_4OAc$ with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

Lipofectin™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 μg/mL per 100 nM oligomeric compound(s). This transfection mixture is incubated at room temperature for approximately 0.5 hours. For cells grown in 96-well plates, wells are washed once with 100 μL OPTI-MEM™-1 and then treated with 130 μL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                          (SEQ ID NO: 2)
Forward primer:    AATGGCTAAGTGAAGATGACAATCAT (SEQ ID NO: 3)
Reverse primer:    TGCACATATCATTACACCAGTTCGT
```

And the PCR probe:

```
                                          (SEQ ID NO: 4)
FAM-TTGCAGCAATTCACTGTAAAGCTGGAAAGG-TAMRA,
``` where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 14

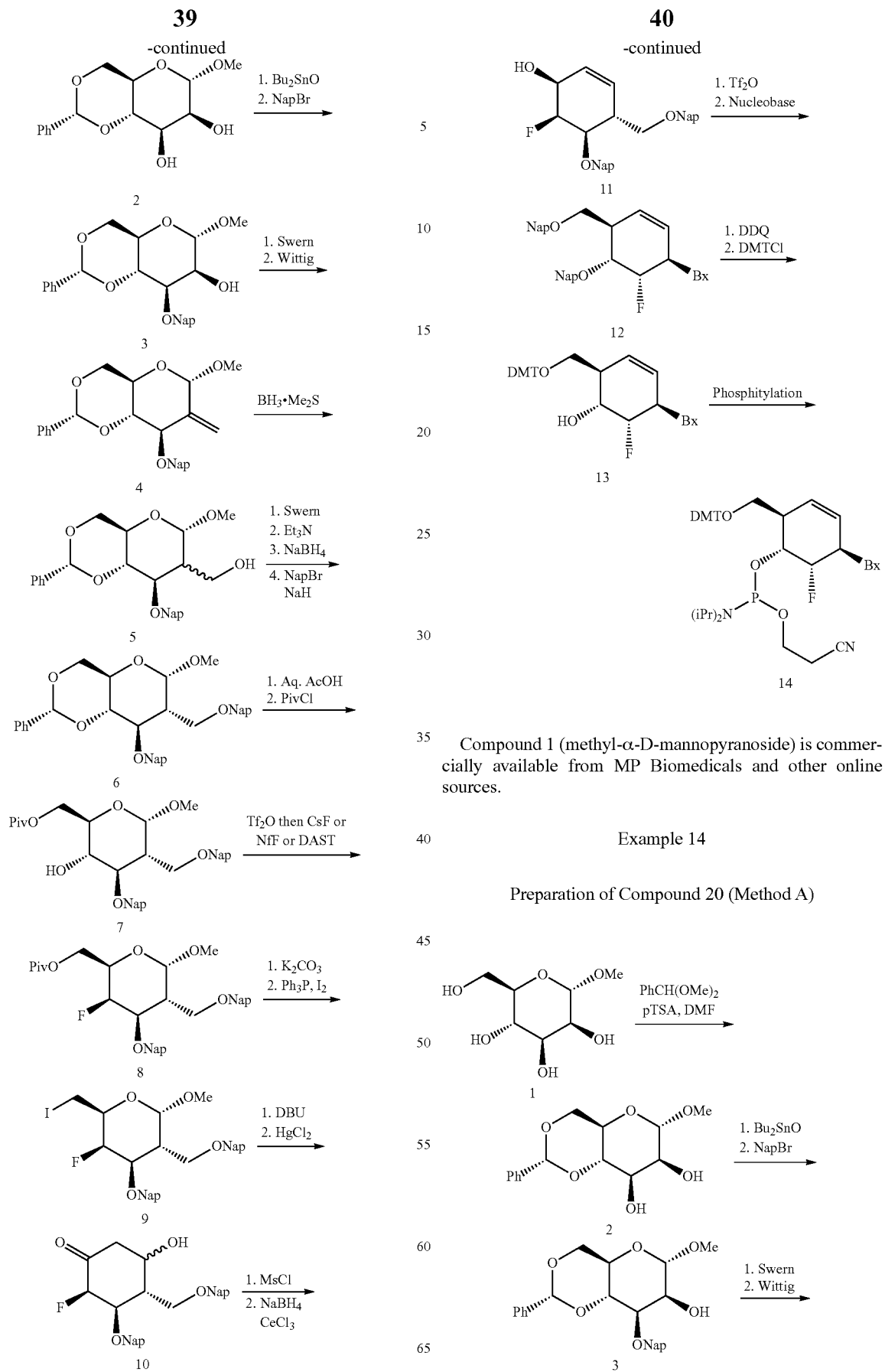
Compound 1 (methyl-α-D-mannopyranoside) is commercially available from MP Biomedicals and other online sources.
Example 14
Preparation of Compound 20 (Method A)

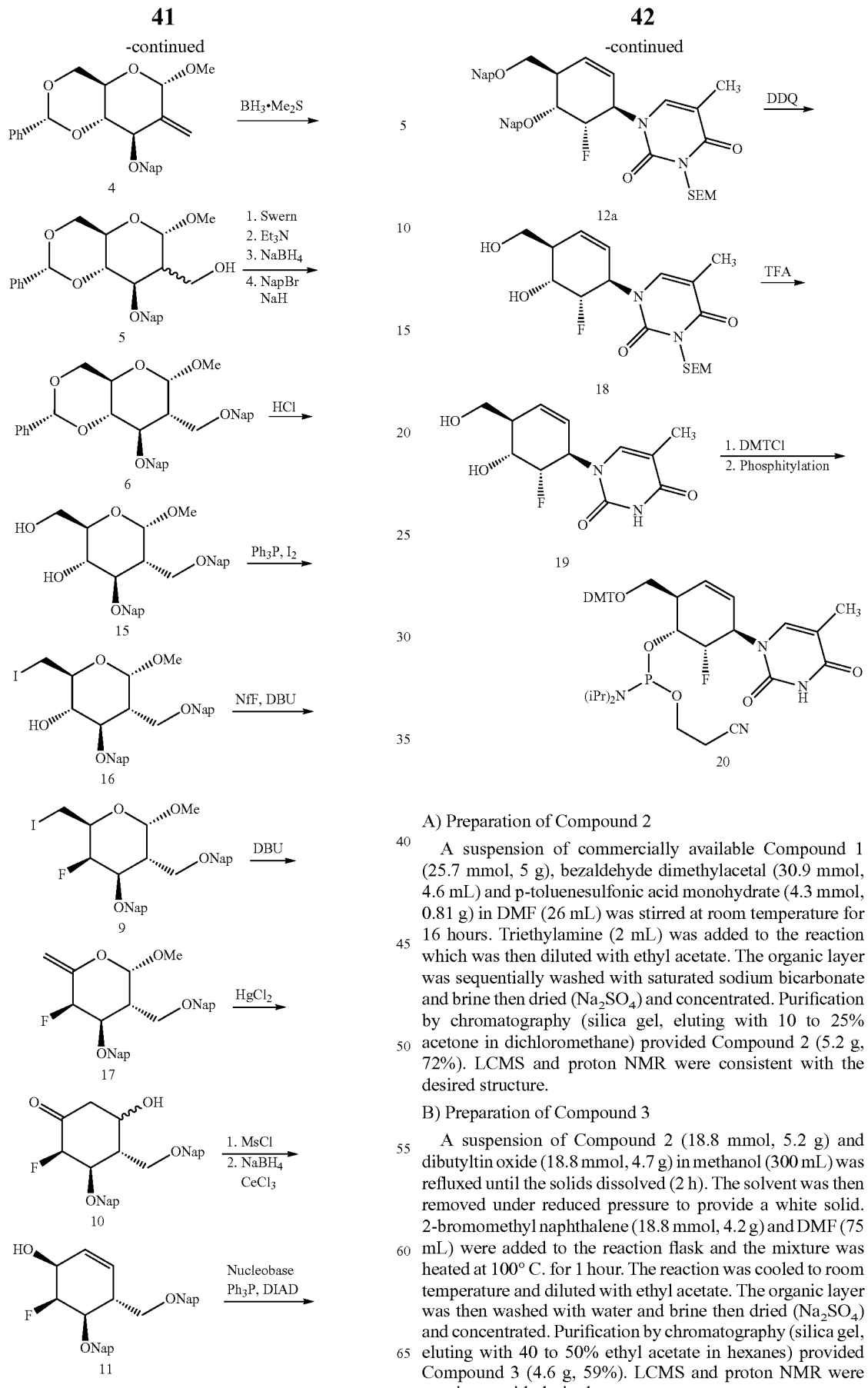

A) Preparation of Compound 2

A suspension of commercially available Compound 1 (25.7 mmol, 5 g), bezaldehyde dimethylacetal (30.9 mmol, 4.6 mL) and p-toluenesulfonic acid monohydrate (4.3 mmol, 0.81 g) in DMF (26 mL) was stirred at room temperature for 16 hours. Triethylamine (2 mL) was added to the reaction which was then diluted with ethyl acetate. The organic layer was sequentially washed with saturated sodium bicarbonate and brine then dried ($Na_2SO_4$) and concentrated. Purification by chromatography (silica gel, eluting with 10 to 25% acetone in dichloromethane) provided Compound 2 (5.2 g, 72%). LCMS and proton NMR were consistent with the desired structure.

B) Preparation of Compound 3

A suspension of Compound 2 (18.8 mmol, 5.2 g) and dibutyltin oxide (18.8 mmol, 4.7 g) in methanol (300 mL) was refluxed until the solids dissolved (2 h). The solvent was then removed under reduced pressure to provide a white solid. 2-bromomethyl naphthalene (18.8 mmol, 4.2 g) and DMF (75 mL) were added to the reaction flask and the mixture was heated at 100° C. for 1 hour. The reaction was cooled to room temperature and diluted with ethyl acetate. The organic layer was then washed with water and brine then dried ($Na_2SO_4$) and concentrated. Purification by chromatography (silica gel, eluting with 40 to 50% ethyl acetate in hexanes) provided Compound 3 (4.6 g, 59%). LCMS and proton NMR were consistent with desired structure.

C) Preparation of Compound 4

Dimethylsulfoxide (28.2 mmol, 2.0 mL) was added to a cold (−78° C.) solution of oxalyl chloride (14.1 mmol, 1.2 mL) in dichloromethane (75 mL). After stirring for 30 minutes a solution of Compound 3 in dichloromethane (35 mL) was added to the reaction and the stirring was continued for another 45 minutes. Triethylamine (42.3 mmol, 5.9 mL) was then added to the reaction and the cooling bath was removed. After stirring for another 30 to 45 minutes, TLC analysis indicated no more starting Compound 3. The reaction was then diluted with dichloromethane and the organic layer was sequentially washed with 5% HCl, saturated sodium bicarbonate, brine, dried ($Na_2SO_4$) and concentrated to provide the crude ketone which was used without any further purification.

nBuLi (16.4 mmol, 6.5 mL of a 2.5 M solution) was added to a cold (0° C.) suspension of methyltriphenylphosphonium bromide (16.4 mmol, 5.8 g) in THF (50 mL). After stirring for 2 hours, the temperature was lowered to −78° C. and a solution of the crude ketone obtained above in THF (20 mL) was added to the reaction which was gradually allowed to warm to room temperature. After stirring for 16 hours, the reaction was quenched with saturated ammonium chloride and the mixture for stirred for 30 minutes. The reaction was then diluted with ethyl acetate and the organic layer was washed with water and brine then dried ($Na_2SO_4$) and concentrated. Purification by chromatography (silica gel, eluting with 10 to 20% ethylacetate in hexanes) provided Compound 4 (3.1 g, 68% from Compound 3). LCMS and proton NMR were consistent with desired structure.

D) Preparation of Compound 5

$BH_3.Me_2S$ (11.1 mmol, 5.6 mL of a 2 M solution in THF) was added to a cold (0° C.) solution of Compound 4 (3.1 g, 7.4 mmol) in THF (120 mL). The reaction was gradually warmed to room temperature and stirred for 16 hours after which it was cooled in an ice bath. The reaction was carefully quenched with sodium hydroxide (3N, 19.5 mL) and hydrogen peroxide (30% solution, 19.5 mL) and then refluxed for 4 hours. The reaction was cooled to room temperature and diluted with ethyl acetate and the organic layer was washed with water and brine then dried ($Na_2SO_4$) and concentrated. Purification by column chromatography (silica gel, eluting with 25 to 40% ethylacetate in hexanes) provided Compound 5 (2 g, 65%). LCMS and proton NMR were consistent with desired structure.

E) Preparation of Compound 6

Dimethylsulfoxide (11.9 mmol, 0.85 mL) was added to a cold (−78° C.) solution of oxalyl chloride (6.0 mmol, 0.52 mL) in dichloromethane (30 mL). After stirring for 30 minutes a solution of Compound 5 in dichloromethane (15 mL) was added to the reaction and the stirring was continued for another 45 minutes. Triethylamine (17.9 mmol, 2.5 mL) was then added to the reaction and the cooling bath was removed. After stirring for another 30 to 45 minutes, TLC analysis indicated no more starting Compound 5. The reaction was then diluted with dichloromethane and the organic layer was sequentially washed with 5% HCl, saturated sodium bicarbonate and brine then dried ($Na_2SO_4$) and concentrated to provide the crude aldehyde which was used without any further purification.

A solution of the crude aldehyde from obtained above and triethylamine (4.6 mmol, 0.65 mL) in dichloromethane (88 mL) was stirred for 3 days at room temperature. Sodium borohydride (100 mg) and methanol (10 mL) were added to the reaction and the stirring was continued for 2 hours at room temperature. The reaction was then concentrated on a rotary evaporator and the residue was diluted with ethyl acetate. The organic layer was sequentially washed with 5% HCl, saturated sodium bicarbonate and brine then dried and concentrated. Purification by column chromatography (silica gel, eluting with 2 to 5% acetone in dichloromethane) provide the primary alcohol (1.55 g, 78%). LCMS and proton NMR were consistent with desired structure.

Sodium hydride (0.2 g, 5.1 mmol, 60% w/w) was added to a cold (0° C.) solution of the primary alcohol from above (1.6 g, 3.6 mmol) and 2-bromomethyl naphthalene (0.9 g, 4.3 mmol) in DMF (10 mL). After stirring for 3 hours, the reaction was carefully quenched with water and diluted with ethyl acetate. The organic layer was washed with water, brine, dried ($Na_2SO_4$) and concentrated. Purification by column chromatography (silica gel, eluting with 0 to 5% acetone in dichloromethane) provided Compound 6 (1.6 g, 80%).

F) Preparation of Compound 15

A solution of Compound 6 (2.6 mmol, 1.5 g) in 1% HCl in methanol (30 mL) was heated at 45° C. for 3 hours after which it was cooled in an ice bath. Sodium borohydride (200 mg) was then added to the reaction and the mixture was stirred for 15 minutes after which it was concentrated to approximately half the original volume on a rotary evaporator. The reaction was then diluted with ethyl acetate and the organic layer was washed with 5% HCl, saturated sodium bicarbonate and brine then dried ($Na_2SO_4$) and concentrated. Purification by column chromatography (silica gel, eluting with 20 to 25% acetone in dichloromethane) provided Compound 15 (1.18 g, 97%). LCMS and proton NMR were consistent with desired structure.

G) Preparation of Compound 16

A suspension of Compound 15 (1.2 mol, 0.6 g), triphenylphosphine (1.8 mmol, 0.48 g), imidazole (3.7 mmol, 0.25 g) and iodine (1.8 mmol, 0.5 g) in toluene (12 mL) was heated at 50° C. for 1 hour. The reaction was cooled to room temperature and quenched with methanol. After stirring for 15 minutes, the reaction was diluted with ethyl acetate and the organic layer was washed with water, sodium thiosulfate and brine then dried ($Na_2SO_4$) and concentrated. Purification by column chromatography (silica gel, eluting with 10 to 25% ethyl acetate in hexanes) provided Compound 16 (0.63 g, 86%). LCMS and proton NMR were consistent with desired structure.

H) Preparation of Compound 9

Nonafluorobutanesulfonyl fluoride (2.5 mmol, 0.44 mL) was added to a cold (0° C.) solution of Compound 16 (0.98 g, 1.6 mmol) and DBU (2.5 mmol, 0.37 mL) in THF (16 mL). The cooling bath was removed and the reaction was stirred at room temperature for 4 hours after which additional nonafluorobutanesulfonyl fluoride (0.15 mL) and DBU (0.13 mL) were added to the reaction. After stirring for an additional 3 hours at room temperature, the reaction was quenched with methanol and diluted with ethyl acetate. The organic layer was then washed with 5% HCl, saturated sodium bicarbonate and brine then dried ($Na_2SO_4$) and concentrated. Purification by chromatography (silica gel, eluting with 10 to 20% ethyl acetate in hexanes) provided Compound 9 (1.0 g, quantitative). LCMS and proton NMR were consistent with desired structure.

I) Preparation of Compound 17

A solution of Compound 9 (0.2 mmol, 0.12 mL) and DBU (10.2 mmol, 1.5 mL) in THF (8.2 mL) was heated at 90° C. for 16 hours after which it was diluted with ethyl acetate. The organic layer was then washed with water, 5% HCl, saturated sodium bicarbonate and brine then dried ($Na_2SO_4$) and concentrated. Purification by chromatography (silica gel, eluting with 10 to 25% ethyl acetate in hexanes) provided Compound 17 (57 mg, 60%). LCMS and proton NMR were consistent with desired structure.

J) Preparation of Compound 10

A suspension of Mercury (II) chloride (0.56 mmol, 0.15 g) and Compound 17 (0.51 mmol, 0.24 g) in acetone (50 mL) and water (25 mL) was refluxed for 2 hours. The solvent was evaporated under reduced pressure and the residue was partitioned between ethyl acetate and water. The organic layer was further washed with brine, dried (Na$_2$SO$_4$) and concentrated. Purification by column chromatography (silica gel, eluting with 50% ethyl acetate in hexanes) provided Compound 10 (0.2 g, 87%). LCMS and proton NMR were consistent with desired structure.

K) Preparation of Compound 11

Methanesulfonyl chloride (2.1 mmol, 0.17 mL) was added to a cold (0° C.) solution of Compound 10 (0.42 mmol, 0.19 g) in pyridine (13 mL). The cooling bath was removed and the reaction was stirred at room temperature for 3 hours after which it was diluted with ethyl acetate and the organic layer was washed with water and brine then dried (Na$_2$SO$_4$) and concentrated to provide a crude residue.

Sodium borohydride (0.84 mmol, 32 mg) was added to a cold (−78° C.) suspension of cerium chloride (115 mg) and the crude residue from above in ethanol (15 mL) and THF (15 mL). After stirring for 15 minutes, the solvents were evaporated under reduced pressure and the residue was redissolved in ethyl acetate. The organic layer was sequentially washed with 5% HCl, saturated sodium bicarbonate and brine then dried (Na$_2$SO$_4$) and concentrated. Purification by column chromatography (silica gel, eluting with 25 to 50% ethyl acetate in hexanes) provided Compound 11 (0.19 g, quantitative). LCMS and proton NMR were consistent with desired structure.

L) Preparation of Compound 12a

DIAD (0.51 mmol, 0.1 mL) was added to a cold (0° C.) solution of Compound 11 (0.34 mmol, 0.15 g), triphenylphosphine (0.51 mmol, 0.13 g) and 3-(2-trimethylsilylethyloxymethyl)-thymine (0.51 mmol, 0.13 g) in THF (3.5 mL). The reaction was gradually warmed to room temperature over 1 hour and then stirred at room temperature for another 3 hours. The reaction was then concentrated under reduced pressure and purified by column chromatography (silica gel, eluting with 10 to 20% ethyl acetate in hexanes) to provide Compound 12a (0.23 g). LCMS and proton NMR were consistent with desired structure.

M) Preparation of Compound 18

DDQ (0.85 mmol, 0.19 g) was added to a biphasic solution of Compound 12a (0.34 mmol, 0.23 g) in dichloromethane (3.4 mL) and water (0.2 mL). After stirring at room temperature for 16 hours, the solvent was removed under reduced pressure and the residue was redissolved in ethyl acetate. The organic layer was then washed with water, 10% sodium bisulfite solution, saturated sodium bicarbonate and brine then dried and concentrated. Purification by chromatography (silica gel, eluting with 10 to 50% acetone in dichloromethane) provided Compound 18 (60 mg). LCMS and proton NMR were consistent with desired structure.

N) Preparation of Compound 20

The SEM group attached to Compound 18 is removed using TFA in dichloromethane to provide Compound 19. Protection of the primary hydroxyl group as the dimethoxytrityl ether followed by a phosphitylation reaction provides Compound 20.

Example 15

Preparation of Compound 20 (Method B)

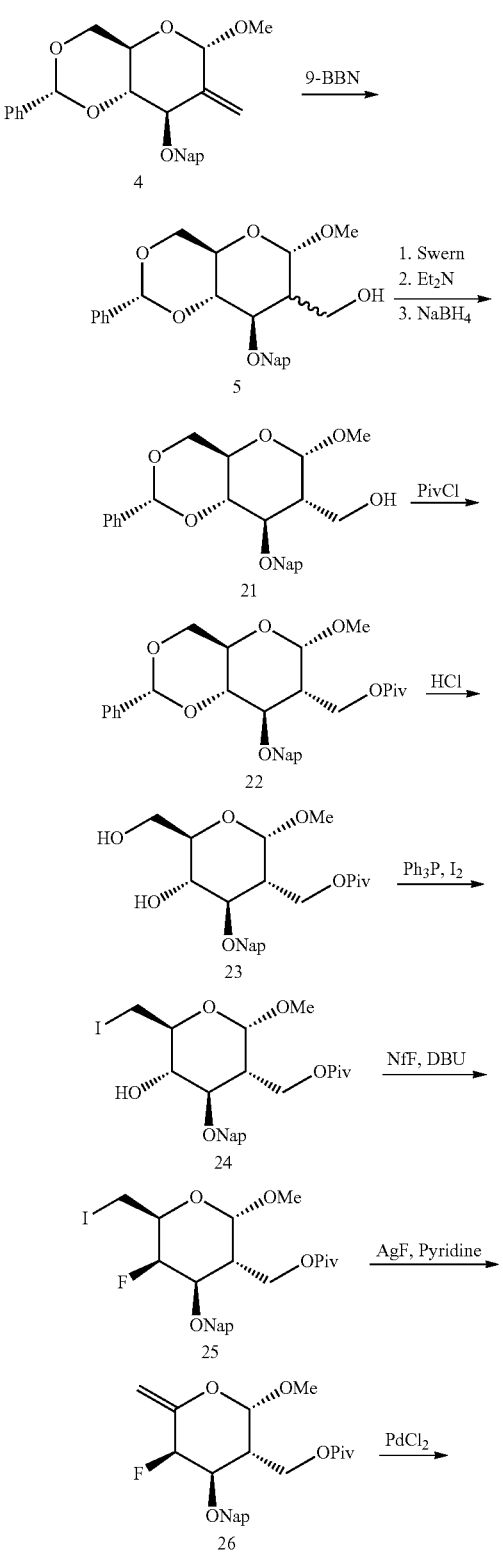

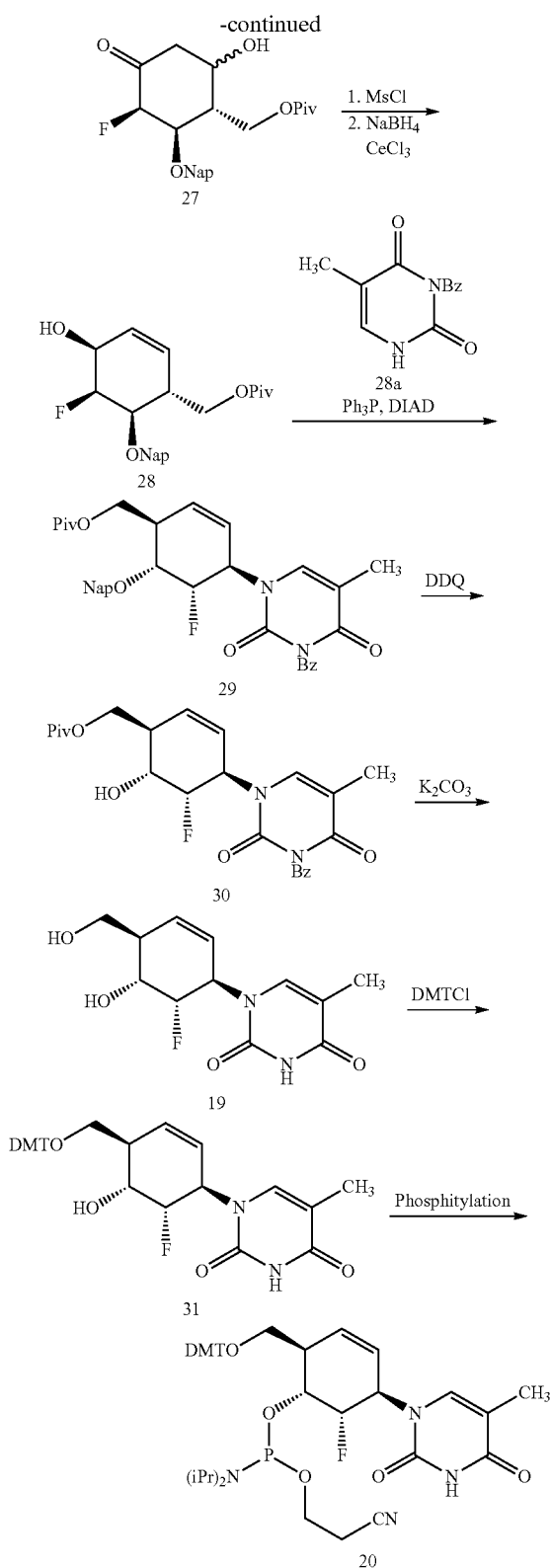

A) Preparation of Compound 5

Compound 4 was prepared as the procedures illustrated in Example 14. 9-BBN (709 mmol, 1419 mL of a 0.5 M solution in THF) was added to a cold (0° C.) solution of Compound 4 (177 mmol, 74 g) in THF (735 mL). The reaction was warmed to 40° C. and stirred for 16 hours. The reaction was carefully quenched with sodium hydroxide (3N, 470 mL) and hydrogen peroxide (30% solution, 470 mL) with ice bath and then stirred at room temperature for 30 minutes. The reaction was diluted with ethyl acetate and the organic layer was washed with water and brine then dried ($Na_2SO_4$) and concentrated. Purification by column chromatography (silica gel, eluting with 33% ethyl acetate in hexanes) provided Compound 5 as a white solid (78 g, quantitative). LCMS; RT: 3.911 min and 4.011 min. MS: m/z=M+23=459.1.

B) Preparation of Compound 21

Dimethylsulfoxide (510 mmol, 36 mL) was added to a cold (−78° C.) solution of oxalyl chloride (254 mmol, 22 mL) in dichloromethane (900 mL). After stirring for 30 minutes a solution of Compound 5 (182 mmol, 79 g) in dichloromethane (600 mL) was added to the reaction and the stirring was continued for another 45 minutes. Triethylamine (760 mmol, 107 mL) was then added to the reaction and the cooling bath was removed. After stirring for another 30 to 45 minutes, TLC analysis indicated no more starting material, Compound 5. The reaction was then diluted with dichloromethane and the organic layer was sequentially washed with 5% HCl, saturated sodium bicarbonate and brine then dried ($Na_2SO_4$) and concentrated to provide the crude aldehyde which was used without any further purification.

A solution of the crude aldehyde obtained from above and triethylamine (228 mmol, 32 mL) in dichloromethane (1000 mL) was stirred for 5 days at room temperature. Sodium borohydride (182 mmol, 6.9 g) and methanol (200 mL) were added to the reaction and the stirring was continued for 12 hours at room temperature. The reaction was then concentrated on a rotary evaporator and the residue was diluted with ethyl acetate. The organic layer was sequentially washed with 5% HCl, saturated sodium bicarbonate and brine then dried and concentrated. Purification by column chromatography (silica gel, eluting with 5 to 10% ethyl acetate in dichloromethane) provided Compound 21 (54 g, 68% over 3 steps). LCMS; RT: 4.020 min. MS: m/z=M+23=459.1.

C) Preparation of Compound 22

PivCl (145 mmol, 17.6 mL) was added to a cold (0° C.) solution of Compound 21 (120 mmol, 53 g), DMAP (12 mmol, 1.5 g) and triethylamine (240 mmol, 34 mL) in dichloromethane (1 L). The reaction was warmed to room temperature and stirred for 12 hours. The reaction was carefully quenched with 1N HCl aqueous solution and neutralized with saturated sodium bicarbonate aqueous solution. The resulting dichloromethane solution was washed with water and brine then dried ($Na_2SO_4$) and concentrated. Purification by column chromatography (silica gel, eluting with 10% ethyl acetate in hexanes) provided Compound 22 as a clear gum (63 g, quantitative). LCMS; RT: 4.725 min. MS: m/z=M+23=543.2.

D) Preparation of Compound 23

A solution of Compound 22 (120 mmol, 63.4 g) in a mixture of 1,4-dioxane (500 mL) and 1% HCl in methanol (500 mL) was heated at 45° C. for 3 hours after which it was cooled in an ice bath. Saturated sodium bicarbonate aqueous solution (500 mL) was then added to the reaction mixture after which organic solvent was removed on a rotary evaporator. The residue was extracted with dichloromethane and the organic layer was washed with brine then dried ($Na_2SO_4$) and concentrated. Purification by column chromatography (silica gel, eluting with to 25% ethyl acetate in hexanes and 5% MeOH in dichloromethane) provided Compound 23 as a white foam (47.7 g, 92%). LCMS; RT: 3.551 min. MS: m/z=M+23=455.

E) Preparation of Compound 24

A suspension of Compound 23 (110 mmol, 47.5 g), triphenylphosphine (120 mmol, 31.8 g), imidazole (240 mmol, 16.5 g) and iodine (120 mmol, 31 g) in toluene (1 L) was heated at 50° C. for 1 hour. The reaction was cooled to room temperature and quenched with saturated $Na_2S_2O_3$. After stirring for 15 minutes, the reaction was diluted with ethyl acetate and the organic layer was washed with brine then dried (Na$_2$SO$_4$) and concentrated. Purification by column chromatography (silica gel, eluting with 10 to 25% ethyl acetate in hexanes) provided Compound 24 as a white foam (56.53 g, 95%). LCMS; RT: 4.438 min. MS: m/z=M+23=565.

F) Preparation of Compound 25

Nonafluorobutanesulfonyl fluoride (207 mmol, 38.6 mL) was added to a cold (0° C.) solution of Compound 24 (103 mmol, 56.2 g) and DBU (207 mmol, 31 mL) in THF (1 L). The cooling bath was removed and the reaction was stirred at room temperature for 2 hours and the reaction was extracted with ethyl acetate. The organic layer was then washed with 5% HCl, saturated sodium bicarbonate and brine then dried (Na$_2$SO$_4$) and concentrated. Purification by chromatography (silica gel, eluting with 10 ethyl acetate in hexanes) provided Compound 25 as a dark yellow gum (56 g, quantitative). LCMS; RT: 4.653 min. MS: m/z=M+23=567.1.

G) Preparation of Compound 26

Compound 26 was prepared as per the procedures published in *Tetrahedron* 2008, 64, 2080 and *Molecules* 2005, 10, 901. A solution of Compound 25 (99.3 mmol, 54.1 g) and AgF (298 mmol, 38 g) in pyridine (1 L) was stirred in the dark at room temperature for 3 days after which it was filtered through a Celite pad and washed with ethyl acetate. The resulting mixture was washed with water, 5% HCl, saturated sodium bicarbonate, brine then dried (Na$_2$SO$_4$) and concentrated. Purification by chromatography (silica gel, eluting with 10 ethyl acetate in hexanes) provided Compound 26 as a light yellow gum (39.65 g, 95%). LCMS; RT: 4.459 min. MS: m/z=M+23=439.

H) Preparation of Compound 27

A suspension of palladium (II) chloride (4.7 mmol, 0.83 g) and Compound 26 (93.3 mmol, 38.9 g) in 1,4-dioxane (600 mL) and water (300 mL) mixture was stirred at 70° C. for 20 minutes. The reaction was cooled to room temperature and extracted with ethyl acetate. The resulting solution was washed with brine, dried (Na$_2$SO$_4$) and concentrated. Purification by column chromatography (silica gel, eluting with 50% ethyl acetate in hexanes) provided Compound 27 as a clear gum (30 g, 80%). LCMS; RT: 3.647 min and 3.869 min. MS: m/z=M+23=457.1 and 425.1.

I) Preparation of Compound 28

Methanesulfonyl chloride (472 mmol, 37 mL) was added to a cold (0° C.) solution of Compound 27 (94.5 mmol, 40.4 g) in pyridine (1 L). The cooling bath was removed and the reaction was stirred at room temperature for one hour after which it was concentrated to provide a crude residue.

Sodium borohydride (189 mmol, 7.2 g) was added to a cold (−78° C.) suspension of cerium chloride (94.5 mmol, 25.8 g) and the crude residue from above in ethanol (700 mL) and THF (700 mL). After stirring for 90 minutes, the solvents were evaporated under reduced pressure and the residue was redissolved in dichloromethane. The organic layer was sequentially washed with 5% HCl, saturated sodium bicarbonate, brine then dried (Na$_2$SO$_4$) and concentrated. Purification by column chromatography (silica gel, eluting with dichloromethane, 10% ethyl acetate in dichloromethane) provided Compound 28 as a yellow gum (12.63 g, 34.5%). LCMS; RT: 3.757 min. MS: m/z=M+23=409.1.

J) Preparation of Compound 29

Compound 28a, 3-N-benzoyl-Thymine was prepared as per the procedures published in *Chinese Chemical Letters* 2005, 16, 287. DIAD (28 mmol, 5.4 mL) was added to a cold (0° C.) solution of Compound 28 (23.3 mmol, 9 g), triphenylphosphine (28 mmol, 7.3 g) and Compound 28a (28 mmol, 6.4 g) in THF (240 mL). The reaction was gradually warmed to room temperature over 1 hour and then stirred at room temperature for another hour. The reaction was then concentrated under reduced pressure and purified by column chromatography (silica gel, eluting with 10% acetone in hexanes) to provide Compound 29 (11 g, 78%). LCMS; RT: 4.321 min. MS: m/z=M+23=621.1.

K) Preparation of Compound 30

DDQ (55.3 mmol, 12.6 g) was added to a biphasic solution of Compound 29 (19.8 mmol, 11.8 g) in dichloromethane (200 mL) and water (10 mL). After stirring at room temperature for 2 hours, the reaction was quenched with 10% sodium bisulfate. The resulting mixture was extracted with dichloromethane. The organic layer was then washed with brine then dried (Na$_2$SO$_4$) and concentrated. Purification by column chromatography (silica gel, eluting with 10% ethyl acetate in dichloromethane) provided Compound 30 (8.64 g, 95%). LCMS; RT: 3.359 min. MS: m/z=M+23=481.1.

L) Preparation of Compound 19

Potassium carbonate (39.8 mmol, 5.5 g) was added to a methanol solution of Compound 30 (16 mmol, 7.3 g). After stirring at room temperature for 12 hours, the reaction was neutralized with acetic acid. The resulting mixture was concentrated to dryness. Purification by column chromatography (silica gel, eluting with 10% MeOH in dichloromethane) provided Compound 19 (3.32 g, 68%). LCMS; RT: 1.324 min. MS: m/z=M+23=293.0.

M) Preparation of Compound 31

DMTCl was added to a cold (0° C.) pyridine (115 mL) solution of Compound 19 (11.5 mmol, 3.1 g). The reaction was then warmed to room temperature and left stirring at room temperature for three hours. The reaction was treated with MeOH (10 mL) with stirring for 30 minutes, then diluted with water and extracted with ethyl acetate. The ethyl acetate solution was washed with brine and concentrated under reduced pressure. Purification by column chromatography (silica gel, eluting with 2-5% MeOH in dichloromethane) provided Compound 31 (6.5 g, quantitative). LCMS; RT: 3.657 min. MS: m/z=M+23=595.2.

N) Preparation of Compound 20

To a dry DMF (29 mL) solution of Compound 31 (5.6 mmol, 3.2 g) and tetrazole (4.5 mmol, 0.31 g) at 0° C., 1-methyl imidazole (1.4 mmol, 0.11 mL) and 2-cyanoethyl-N,N,N',N'-tetraisopropyl phosphorodiamidite (8.4 mmol, 2.7 mL) were added. The reaction was then warmed to room temperature and left stirring at room temperature for two hours. The reaction was quenched with saturated sodium bicarbonate and extracted with ethyl acetate. The ethyl acetate solution was washed with brine then dried (Na$_2$SO$_4$) and concentrated under reduced pressure. Purification by column chromatography (silica gel, eluting with 33% ethyl acetate in hexanes) provided Compound 20 (3.88 g, 90%). $^{31}$P NMR: 151.61, 151.46, 150.92, 150.84 ppm. MS: m/z=M+1=773.

Example 16

Preparation of Compound 36

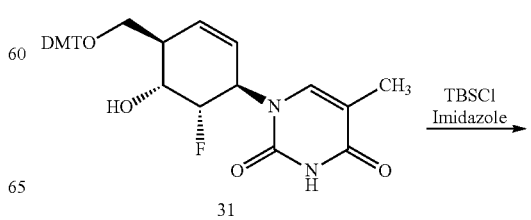

31

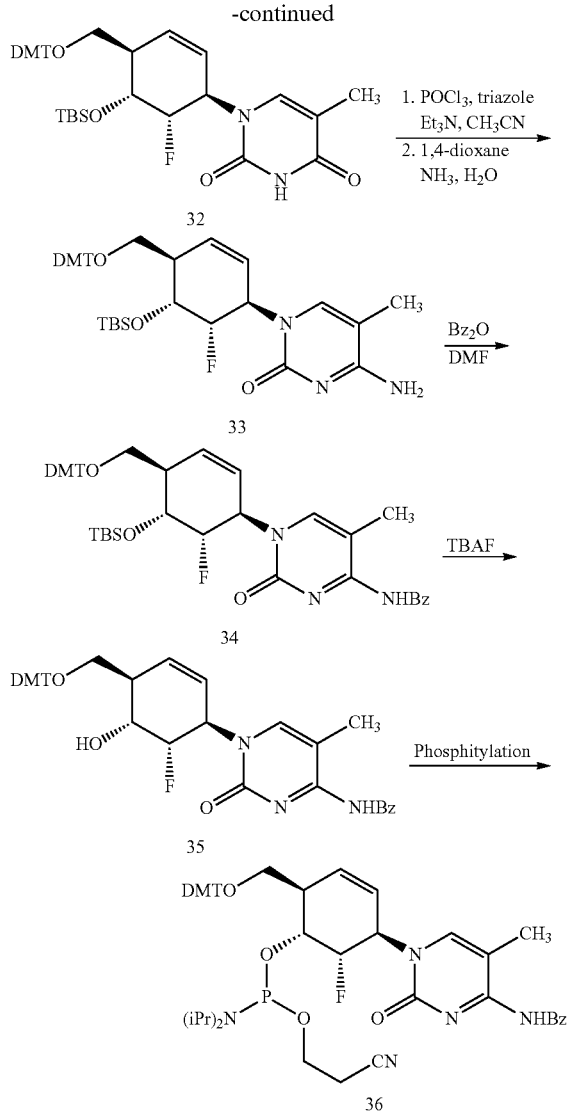

A) Preparation of Compound 32

Compound 31 was prepared as per the procedures illustrated in Example 15. tert-butyldimethylsilyl chloride (16.9 mmol, 2.93 mL) was added to a cold (0° C.) solution of Compound 31 (6.75 mmol, 3.86 g) and imidazole (43.8 mmol, 2.99 g) in anhydrous DMF (60 mL). The reaction was warmed to room temperature and stirred for 16 hours. The reaction mixture was quenched with saturated sodium bicarbonate and diluted with diethyl ether. The organic layer was washed with brine then dried ($Na_2SO_4$) and concentrated under reduced pressure. Purification by column chromatography (silica gel, eluting with 1% methanol in dichloromethane) provided Compound 32 (3.51 g, 76%). LCMS; RT: 4.839 min. MS: m/z=M+23=709.

B) Preparation of Compound 33

$POCl_3$ (40 mmol, 3.66 mL) was added to a cold (0° C.) suspension of 1,2,4-triazole (160 mmol, 11 g) in anhydrous $CH_3CN$ (40 mL). After stirring for 15 minutes, triethylamine was added and the stirring was continued for another 30 minutes. A solution of Compound 32 (6.73 mmol, 2.62 g) in $CH_3CN$ was cannulated to the cold reaction mixture and remained 0° C. for an additional 20 minutes. The reaction was then concentrated under reduced pressure after 2 hours of stirring at room temperature and redissolved in dichloromethane. The resulting mixture was diluted with dichloromethane and the organic layer was washed with brine then dried ($Na_2SO_4$) and concentrated under reduced pressure. The residue was redissolved in 1,4-dioxane (50 mL) and was added to a cold (0° C.) solution of $NH_3.H_2O$ (27 mL of 32% aqueous solution). The reaction mixture was allowed to gradually warm to room temperature and left stirring overnight. The reaction was quenched with water and diluted with diethyl ether. The organic layer was washed with brine then dried ($Na_2SO_4$) and concentrated under reduced pressure. Purification by column chromatography (silica gel, eluting with 2% methanol in dichloromethane) provided Compound 33 (3.0 g, 87%). LCMS; RT: 4.073 min. MS: m/z=M+1=687.

C) Preparation of Compound 34

Benzoic anhydride (5.51 mmol, 1.25 g) was added to a cold (0° C.) solution of Compound 33 (4.24 mmol, 2.90 g) in anhydrous DMF (40 mL) and was allowed to gradually warm to room temperature. After stirring for 36 hours, the reaction mixture was quenched with saturated sodium bicarbonate and diluted with ethyl acetate. The organic layer was washed with brine then dried ($Na_2SO_4$) and concentrated. Purification by column chromatography (silica gel, eluting with 10% ethyl acetate in hexanes) provided Compound 34 (3.02 g, 90%). LCMS; RT: 5.517 min. MS: m/z=M+23=812.

D) Preparation of Compound 35

TBAF (4.6 mmol, 46 mL of 1.0 M THF solution) was added to a cold (0° C.) solution of Compound 34 (3.8 mmol, 3.0 g) in THF (46 mL) and was allowed to gradually warm to room temperature. After stirring for 70 minutes, the reaction mixture was quenched with water and diluted with ethyl acetate. The organic layer was washed with brine then dried ($Na_2SO_4$) and concentrated. Purification by column chromatography (silica gel, eluting with 33% ethyl acetate in hexanes) provided Compound 35 (2.4 g, 93%). LCMS; RT: 4.489 min. MS: m/z=M+23=698.2.

E) Preparation of Compound 36

1-methyl imidazole (0.87 mmol, 0.069 mL) and 2-cyanoethyl-N,N,N',N'-tetraisopropyl phosphorodiamidite (5.2 mmol, 1.67 mL) were added to a cold (0° C.) solution of Compound 35 (3.5 mmol, 2.35 g) and tetrazole (2.8 mmol, 0.2 g) in anhydrous DMF (18 mL) and the reaction was allowed to gradually warm to room temperature. After stirring for five hours, the reaction mixture was quenched with saturated sodium bicarbonate and diluted with ethyl acetate. The organic layer was washed with brine then dried ($Na_2SO_4$) and concentrated. Purification by column chromatography (silica gel, eluting with 33% ethyl acetate in hexanes) provided Compound 36 (2.6 g, 95%). $^{31}P$ NMR: 151.63, 151.48, 150.86, 150.78 ppm. MS: m/z=M+1=876.

Example 17

Preparation of Compound 41

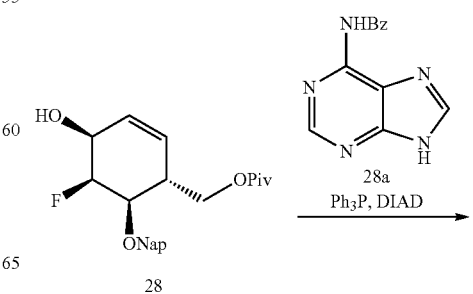

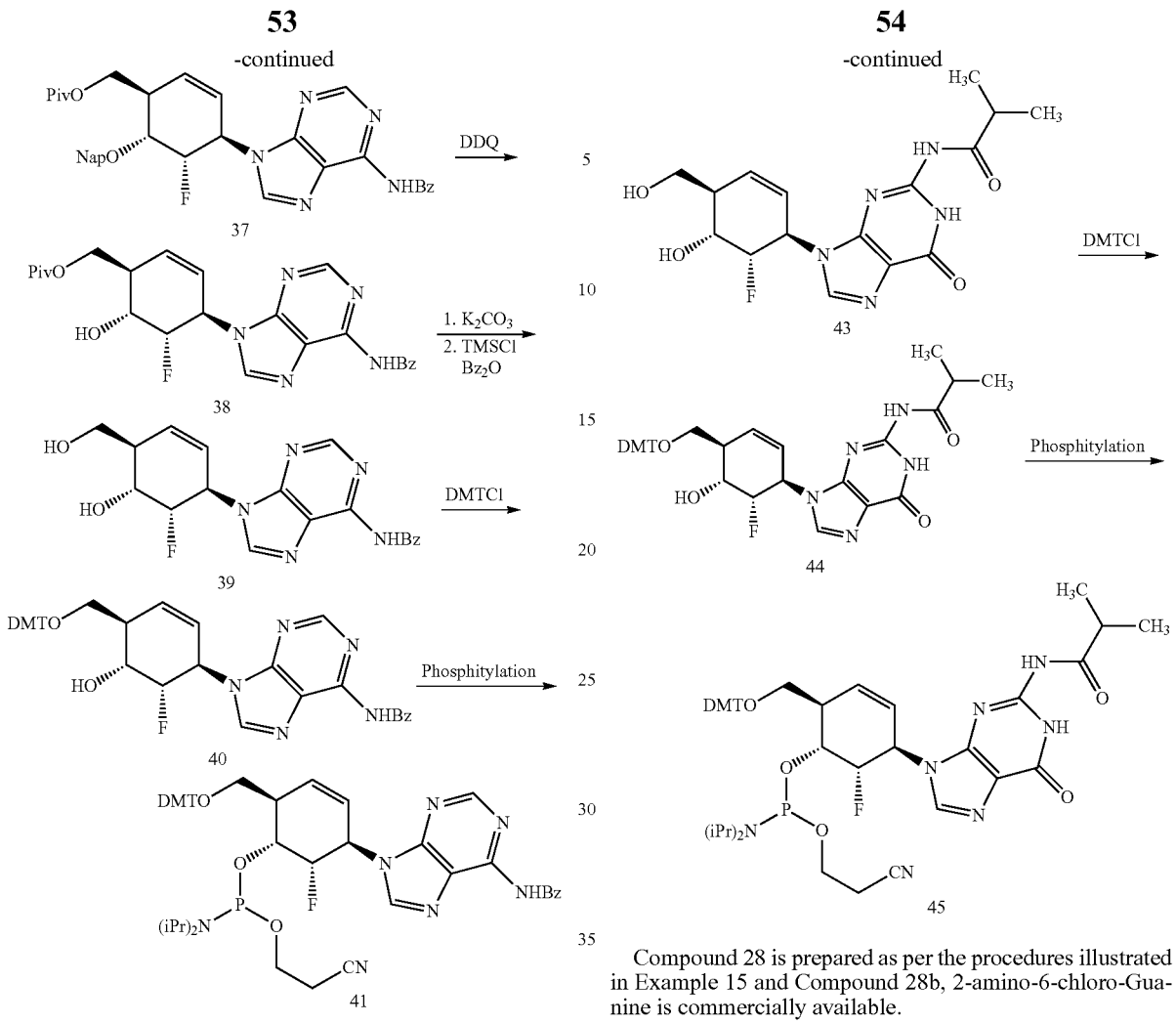

Compound 28 is prepared as per the procedures illustrated in Example 15 and Compound 28a, N-benzoyl Adenine is commercially available.

Example 18

Preparation of Compound 45

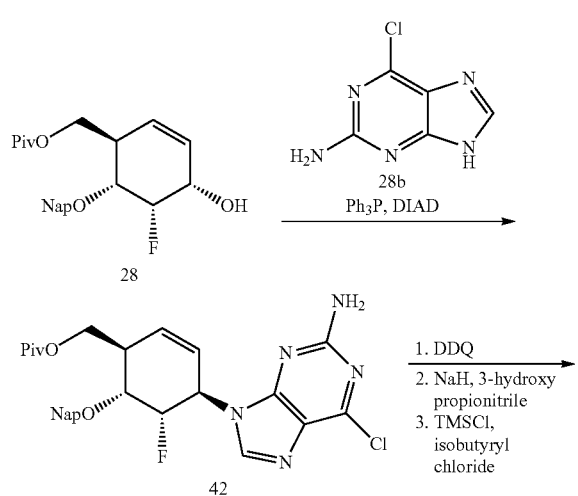

Compound 28 is prepared as per the procedures illustrated in Example 15 and Compound 28b, 2-amino-6-chloro-Guanine is commercially available.

Example 19

Preparation of Oligomeric Compounds

Following synthetic procedures well know in the art, some of which are illustrated herein, oligomeric compounds are prepared having at least one cyclohexenyl nucleic acid analog of Formula III, using one or more of the phosphoramidite compounds illustrated in the Examples such as DMT phosphoramidite, Compound 14, Example 13.

Example 20

3-10-3 Gapped Oligomeric Compounds Targeted to PTEN

In Vivo Study

Six week old Balb/c mice (Jackson Laboratory, Bar Harbor, Me.) were injected with a single dose of ASOs 464846 and 464847 targeted to PTEN at a dose of 3.2, 10, 32 and 100 mg/kg. The mice were sacrificed 48 hours following the last administration. Liver tissues were homogenized and mRNA levels were quantitated using real-time PCR using procedures illustrated herein for comparison to untreated control levels (% UTC). Plasma chemistry analysis was also completed. Tms were determined in 100 mM phosphate buffer, 0.1 mM EDTA, pH 7, at 260 nm using 4 μM of the gapped oligomeric compounds listed below and 4 μM of the complementary RNA. Estimated $ED_{50}$ concentrations for each gapped oligomeric compound were calculated using Graphpad Prism and the results are summarized below:

| SEQ ID NO./ ISIS NO. | Composition (5' to 3') | ED50 (mg/kg) | Tm (° C.) vs. 20-mer RNA |
|---|---|---|---|
| 05/464846 | $T_e{}^mC_eT_e$TAG$^m$CA$^m$CTGGC$^m$C$_eT_eT_e$ | 91 | 62.35 |
| 05/464847 | $T_f{}^mC_fT_f$TAG$^m$CA$^m$CTGGC$^m$C$_fT_fT_f$ | 22 | 64.37 |

Each internucleoside linking group is a phosphorothioate and superscript Me indicates a 5-methyl group on the heterocyclic base (Bx). Subscripted nucleosides are defined below:

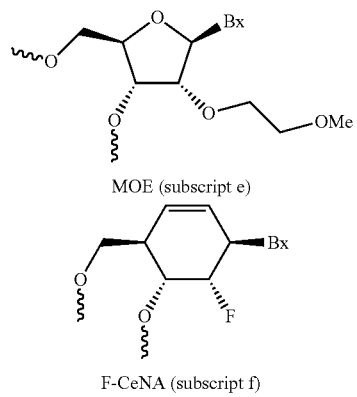

MOE (subscript e)

F-CeNA (subscript f)

Liver transaminase levels, alanine aminotranferease (ALT) and aspartate aminotransferase (AST), in serum were also measured relative to saline injected mice. The approximate liver transaminase levels are listed in the table below.

| SEQ ID NO./ ISIS NO. | ALT @ 3.2 mg/kg | ALT @ 10 mg/kg | ALT @ 32 mg/kg | ALT @ 100 mg/kg |
|---|---|---|---|---|
| 05/464846 | 38 | 25 | 22 | 22 |
| 05/464847 | 24 | 23 | 24 | 284 |

All publications, patents, and patent applications referenced herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A cyclohexenyl nucleic acid analog having Formula I:

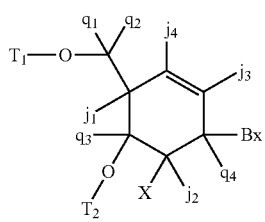

wherein:
Bx is a heterocyclic base moiety selected from uracil, thymine, cytosine, 5-methyl-cytosine, adenine and guanine wherein exocyclic amino groups are optionally protected;
X is fluoro;
one of $T_1$ and $T_2$ is H or a hydroxyl protecting group and the other of $T_1$ and $T_2$ is H, a hydroxyl protecting group or a reactive phosphorus group;
$q_1$, $q_2$, $q_3$ and $q_4$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
$j_1$, $j_2$, $j_3$ and $j_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl; and wherein each substituted group is, independently, mono or poly substituted with optionally protected substituent groups independently selected from halogen, oxo, hydroxyl, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl.

2. The cyclohexenyl nucleic acid analog of claim 1 wherein $q_1$, $q_2$, $q_3$ and $q_4$ are each H.

3. The cyclohexenyl nucleic acid analog of claim 1 wherein at least one of $q_1$, $q_2$, $q_3$ and $q_4$ is substituted $C_1$-$C_6$ alkyl.

4. The cyclohexenyl nucleic acid analog of claim 1 wherein at least one of $q_1$, $q_2$, $q_3$ and $q_4$ is substituted $C_1$-$C_6$ alkyl comprising at least one substituent group selected from fluoro or $OCH_3$.

5. The cyclohexenyl nucleic acid analog of claim 1 wherein at least one of $q_1$, $q_2$, $q_3$ and $q_4$ is $C_1$-$C_6$ alkyl.

6. The cyclohexenyl nucleic acid analog of claim 1 wherein at least one of $q_1$, $q_2$, $q_3$ and $q_4$ is methyl.

7. The cyclohexenyl nucleic acid analog of claim 1 wherein $j_1$, $j_2$, $j_3$ and $j_4$ are each H.

8. The cyclohexenyl nucleic acid analog of claim 1 wherein at least one of $j_1$, $j_2$, $j_3$ and $j_4$ is substituted $C_1$-$C_6$ alkyl.

9. The cyclohexenyl nucleic acid analog of claim 1 wherein at least one of $j_1$, $j_2$, $j_3$ and $j_4$ is substituted $C_1$-$C_6$ alkyl comprising at least one substituent group selected from fluoro or $OCH_3$.

10. The cyclohexenyl nucleic acid analog of claim 1 wherein at least one of $j_1$, $j_2$, $j_3$ and $j_4$ is $C_1$-$C_6$ alkyl.

11. The cyclohexenyl nucleic acid analog of claim 1 wherein at least one of $j_1$, $j_2$, $j_3$ and $j_4$ is methyl or fluoro.

12. The cyclohexenyl nucleic acid analog of claim 1 wherein at least one of $j_1$, $j_2$, $j_3$ and $j_4$ is fluoro.

13. The cyclohexenyl nucleic acid analog of claim 1 wherein $q_1$, $q_2$, $q_3$, $q_4$, $j_1$, $j_2$, $j_3$ and $j_4$ are each H.

14. The cyclohexenyl nucleic acid analog of claim 13 wherein X and $J_2$ are each fluoro.

15. The cyclohexenyl nucleic acid analog of claim 13 having Formula II:

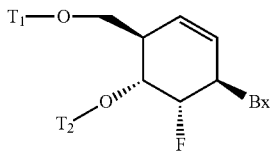

wherein:
Bx is a heterocyclic base moiety; and
one of $T_1$ and $T_2$ is H or a hydroxyl protecting group and the other of $T_1$ and $T_2$ is H, a hydroxyl protecting group or a reactive phosphorus group.

16. The cyclohexenyl nucleic acid analog of claim 1 wherein $T_1$ is selected from acetyl, benzyl, t-butyldimethylsilyl, t-butyldiphenylsilyl and dimethoxytrityl.

17. The cyclohexenyl nucleic acid analog of claim 1 wherein $T_1$ is 4,4'-dimethoxytrityl.

18. The cyclohexenyl nucleic acid analog of claim 1 wherein $T_2$ is a reactive phosphorus group.

19. The cyclohexenyl nucleic acid analog of claim 1 wherein $T_2$ is a reactive phosphorus group selected from diisopropylcyanoethoxy phosphoramidite and H-phosphonate.

20. The cyclohexenyl nucleic acid analog of claim 1 wherein $T_1$ is 4,4'-dimethoxytrityl and $T_2$ is diisopropylcyanoethoxy phosphoramidite.

* * * * *